United States Patent
Brauker et al.

(10) Patent No.: US 9,532,741 B2
(45) Date of Patent: *Jan. 3, 2017

(54) MEMBRANE FOR USE WITH IMPLANTABLE DEVICES

(71) Applicant: DexCom, Inc., San Diego, CA (US)

(72) Inventors: James H. Brauker, Addison, MI (US); Mark C. Shults, Madison, WI (US); Mark A. Tapsak, Orangeville, PA (US)

(73) Assignee: DexCom, Inc., San Diego, CA (US)

( * ) Notice: Subject to any disclaimer, the term of this patent is extended or adjusted under 35 U.S.C. 154(b) by 7 days.

This patent is subject to a terminal disclaimer.

(21) Appl. No.: 14/341,468

(22) Filed: Jul. 25, 2014

(65) Prior Publication Data

US 2014/0335343 A1 Nov. 13, 2014

Related U.S. Application Data

(63) Continuation of application No. 12/633,578, filed on Dec. 8, 2009, now Pat. No. 8,840,552, which is a
(Continued)

(51) Int. Cl.
*A61B 5/145* (2006.01)
*A61B 5/1473* (2006.01)
(Continued)

(52) U.S. Cl.
CPC ........... *A61B 5/14735* (2013.01); *A61B 5/076* (2013.01); *A61B 5/14532* (2013.01);
(Continued)

(58) Field of Classification Search
CPC .............. A61B 5/14532; A61B 5/1468; A61B 5/14865; A61B 5/14546; A61B 5/1473; A61B 5/14735; A61B 5/145; A61B 5/14503
See application file for complete search history.

(56) References Cited

U.S. PATENT DOCUMENTS 3,775,182 A 11/1973 Patton et al.
3,898,984 A 8/1975 Mandel et al.
(Continued)

FOREIGN PATENT DOCUMENTS

EP 0 098 592 1/1984
EP 0 107 634 5/1984
(Continued)

OTHER PUBLICATIONS

Aalders et al., 1991. Development of a wearable glucose sensor; studies in healthy volunteers and in diabetic patients. The International Journal of Artificial Organs 14(2):102-108.
(Continued)

*Primary Examiner* — Eric Winakur
(74) *Attorney, Agent, or Firm* — Knobbe Martens Olson & Bear, LLP

(57) ABSTRACT

The present invention provides a biointerface membrane for use with an implantable device that interferes with the formation of a barrier cell layer including; a first domain distal to the implantable device wherein the first domain supports tissue attachment and interferes with barrier cell layer formation and a second domain proximal to the implantable device wherein the second domain is resistant to cellular attachment and is impermeable to cells. In addition, the present invention provides sensors including the biointerface membrane, implantable devices including these sensors or biointerface membranes, and methods of monitoring glucose levels in a host utilizing the analyte detection implantable device of the invention. Other implantable devices which include the biointerface membrane of the present invention, such as devices for cell transplantation, drug delivery devices, and electrical signal delivery or measuring devices are also provided.

7 Claims, 9 Drawing Sheets

Related U.S. Application Data continuation of application No. 10/768,889, filed on Jan. 29, 2004, now Pat. No. 7,632,228, which is a continuation of application No. 09/916,386, filed on Jul. 27, 2001, now Pat. No. 6,702,857.

(51) Int. Cl.
*A61B 5/07* (2006.01)
*A61B 5/1486* (2006.01)
*A61L 31/10* (2006.01)
*A61L 31/14* (2006.01)

(52) U.S. Cl.
CPC ...... *A61B 5/14546* (2013.01); *A61B 5/14865* (2013.01); *A61L 31/10* (2013.01); *A61L 31/14* (2013.01); *A61B 2562/02* (2013.01); *Y10T 428/249921* (2015.04)

(56) References Cited

U.S. PATENT DOCUMENTS

| | | |
|---|---|---|
| 3,929,971 A | 12/1975 | Roy |
| 3,943,918 A | 3/1976 | Lewis |
| 3,964,974 A | 6/1976 | Banauch et al. |
| 3,966,580 A | 6/1976 | Janata et al. |
| 3,979,274 A | 9/1976 | Newman |
| 4,024,312 A | 5/1977 | Korpman |
| 4,040,908 A | 8/1977 | Clark, Jr. |
| 4,073,713 A | 2/1978 | Newman |
| 4,076,656 A | 2/1978 | White et al. |
| 4,172,770 A | 10/1979 | Semersky et al. |
| 4,197,840 A | 4/1980 | Beck et al. |
| 4,215,703 A | 8/1980 | Willson |
| 4,225,410 A | 9/1980 | Pace |
| 4,240,889 A | 12/1980 | Yoda et al. |
| 4,253,469 A | 3/1981 | Aslan |
| 4,255,500 A | 3/1981 | Hooke |
| 4,259,540 A | 3/1981 | Sabia |
| 4,260,725 A | 4/1981 | Keogh et al. |
| 4,273,636 A | 6/1981 | Shimada et al. |
| 4,340,458 A | 7/1982 | Lerner et al. |
| 4,353,368 A | 10/1982 | Slovak et al. |
| 4,353,888 A | 10/1982 | Sefton |
| 4,374,013 A | 2/1983 | Enfors |
| 4,388,166 A | 6/1983 | Suzuki et al. |
| 4,403,984 A | 9/1983 | Ash et al. |
| 4,415,666 A | 11/1983 | D'Orazio et al. |
| 4,418,148 A | 11/1983 | Oberhardt |
| 4,431,004 A | 2/1984 | Bessman et al. |
| 4,436,094 A | 3/1984 | Cerami |
| 4,442,841 A | 4/1984 | Uehara et al. |
| 4,453,537 A | 6/1984 | Spitzer |
| 4,477,314 A | 10/1984 | Richter et al. |
| 4,484,987 A | 11/1984 | Gough |
| 4,494,950 A | 1/1985 | Fischell |
| 4,506,680 A | 3/1985 | Stokes |
| RE31,916 E | 6/1985 | Oswin et al. |
| 4,534,355 A | 8/1985 | Potter |
| 4,554,927 A | 11/1985 | Fussell |
| 4,571,292 A | 2/1986 | Liu et al. |
| 4,577,642 A | 3/1986 | Stokes |
| 4,603,152 A | 7/1986 | Laurin et al. |
| 4,650,547 A | 3/1987 | Gough |
| 4,663,824 A | 5/1987 | Kenmochi |
| 4,671,288 A | 6/1987 | Gough |
| 4,680,268 A | 7/1987 | Clark, Jr. |
| 4,686,044 A | 8/1987 | Behnke et al. |
| 4,689,309 A | 8/1987 | Jones |
| 4,702,732 A | 10/1987 | Powers et al. |
| 4,703,756 A | 11/1987 | Gough et al. |
| 4,711,251 A | 12/1987 | Stokes |
| 4,721,677 A | 1/1988 | Clark |
| 4,731,726 A | 3/1988 | Allen |
| 4,753,652 A | 6/1988 | Langer et al. |
| 4,757,022 A | 7/1988 | Shults et al. |
| 4,759,828 A | 7/1988 | Young et al. |
| 4,776,944 A | 10/1988 | Janata et al. |
| 4,781,798 A | 11/1988 | Gough |
| 4,787,398 A | 11/1988 | Garcia et al. |
| 4,803,243 A | 2/1989 | Fujimoto et al. |
| 4,805,624 A | 2/1989 | Yao et al. |
| 4,805,625 A | 2/1989 | Wyler |
| 4,810,470 A | 3/1989 | Burkhardt et al. |
| 4,823,808 A | 4/1989 | Clegg et al. |
| 4,852,573 A | 8/1989 | Kennedy |
| 4,861,830 A | 8/1989 | Ward, Jr. |
| 4,871,440 A | 10/1989 | Nagata et al. |
| 4,883,057 A | 11/1989 | Broderick |
| 4,889,744 A | 12/1989 | Quaid |
| 4,890,620 A | 1/1990 | Gough |
| 4,902,294 A | 2/1990 | Gosserez |
| 4,927,407 A | 5/1990 | Dorman |
| 4,935,345 A | 6/1990 | Guilbeau et al. |
| 4,953,552 A | 9/1990 | DeMarzo |
| 4,963,595 A | 10/1990 | Ward et al. |
| 4,970,145 A | 11/1990 | Bennetto et al. |
| 4,984,929 A | 1/1991 | Rock et al. |
| 4,986,271 A | 1/1991 | Wilkins |
| 4,986,671 A | 1/1991 | Sun et al. |
| 4,988,341 A | 1/1991 | Columbus et al. |
| 4,994,167 A | 2/1991 | Shults et al. |
| 5,002,572 A | 3/1991 | Picha |
| 5,007,929 A | 4/1991 | Quaid |
| 5,019,096 A | 5/1991 | Fox, Jr. et al. |
| 5,050,612 A | 9/1991 | Matsumura |
| 5,059,654 A | 10/1991 | Hou et al. |
| 5,067,491 A | 11/1991 | Taylor, II et al. |
| 5,101,814 A | 4/1992 | Palti |
| 5,108,819 A | 4/1992 | Heller et al. |
| 5,113,871 A | 5/1992 | Viljanto et al. |
| 5,130,231 A | 7/1992 | Kennedy et al. |
| 5,137,028 A | 8/1992 | Nishimura |
| 5,160,418 A | 11/1992 | Mullen |
| 5,165,407 A | 11/1992 | Wilson et al. |
| 5,171,689 A | 12/1992 | Kawaguri et al. |
| 5,190,041 A | 3/1993 | Palti |
| 5,222,980 A | 6/1993 | Gealow |
| 5,235,003 A | 8/1993 | Ward et al. |
| 5,249,576 A | 10/1993 | Goldberger et al. |
| 5,264,104 A | 11/1993 | Gregg et al. |
| 5,269,891 A | 12/1993 | Colin |
| 5,271,736 A | 12/1993 | Picha |
| 5,282,848 A | 2/1994 | Schmitt |
| 5,285,513 A | 2/1994 | Kaufman et al. |
| 5,299,571 A | 4/1994 | Mastrototaro |
| 5,304,468 A | 4/1994 | Phillips et al. |
| 5,310,469 A | 5/1994 | Cunningham et al. |
| 5,314,471 A | 5/1994 | Brauker et al. |
| 5,316,008 A | 5/1994 | Suga et al. |
| 5,321,414 A | 6/1994 | Alden et al. |
| 5,322,063 A | 6/1994 | Allen et al. |
| 5,324,322 A | 6/1994 | Grill, Jr. et al. |
| 5,326,356 A | 7/1994 | Della Valle et al. |
| 5,328,451 A | 7/1994 | Davis et al. |
| 5,330,521 A | 7/1994 | Cohen |
| 5,331,555 A | 7/1994 | Hashimoto et al. |
| 5,340,352 A | 8/1994 | Nakanishi et al. |
| 5,342,409 A | 8/1994 | Mullett |
| 5,343,869 A | 9/1994 | Pross et al. |
| 5,344,454 A | 9/1994 | Clarke et al. |
| 5,348,788 A | 9/1994 | White |
| 5,356,786 A | 10/1994 | Heller et al. |
| 5,368,028 A | 11/1994 | Palti |
| 5,372,133 A | 12/1994 | Hogen Esch |
| 5,380,536 A | 1/1995 | Hubbell et al. |
| 5,384,028 A | 1/1995 | Ito |
| 5,387,327 A | 2/1995 | Khan |
| 5,390,671 A | 2/1995 | Lord et al. |
| 5,391,250 A | 2/1995 | Cheney, II et al. |
| 5,397,848 A | 3/1995 | Yang et al. |
| 5,411,647 A | 5/1995 | Johnson et al. |
| 5,417,395 A | 5/1995 | Fowler et al. |
| 5,421,923 A | 6/1995 | Clarke et al. |
| 5,428,123 A | 6/1995 | Ward et al. |

(56) References Cited

U.S. PATENT DOCUMENTS

| | | |
|---|---|---|
| 5,429,735 A | 7/1995 | Johnson et al. |
| 5,431,160 A | 7/1995 | Wilkins |
| 5,453,278 A | 9/1995 | Chan et al. |
| 5,458,631 A | 10/1995 | Xavier et al. |
| 5,462,051 A | 10/1995 | Oka et al. |
| 5,462,064 A | 10/1995 | D'Angelo et al. |
| 5,464,013 A | 11/1995 | Lemelson |
| 5,466,356 A | 11/1995 | Schneider et al. |
| 5,469,846 A | 11/1995 | Khan |
| 5,476,094 A | 12/1995 | Allen et al. |
| 5,480,711 A | 1/1996 | Ruefer |
| 5,484,404 A | 1/1996 | Schulman et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,507,288 A | 4/1996 | Bocker et al. |
| 5,508,030 A | 4/1996 | Bierman |
| 5,513,636 A | 5/1996 | Palti |
| 5,518,601 A | 5/1996 | Foos et al. |
| 5,529,066 A | 6/1996 | Palti |
| 5,531,878 A | 7/1996 | Vadgama et al. |
| 5,538,511 A | 7/1996 | Van Antwerp |
| 5,540,828 A | 7/1996 | Yacynych |
| 5,545,220 A | 8/1996 | Andrews et al. |
| 5,545,223 A | 8/1996 | Neuenfeldt et al. |
| 5,549,675 A | 8/1996 | Neuenfeldt et al. |
| 5,564,439 A | 10/1996 | Picha |
| 5,568,806 A | 10/1996 | Cheney, II et al. |
| 5,569,186 A | 10/1996 | Lord et al. |
| 5,569,462 A | 10/1996 | Martinson et al. |
| 5,571,395 A | 11/1996 | Park et al. |
| 5,575,930 A | 11/1996 | Tietje-Girault et al. |
| 5,578,463 A | 11/1996 | Berka et al. |
| 5,582,184 A | 12/1996 | Erickson et al. |
| 5,584,813 A | 12/1996 | Livingston et al. |
| 5,584,876 A | 12/1996 | Bruchman et al. |
| 5,586,553 A | 12/1996 | Halili et al. |
| 5,589,133 A | 12/1996 | Suzuki |
| 5,589,563 A | 12/1996 | Ward et al. |
| 5,590,651 A | 1/1997 | Shaffer et al. |
| 5,593,440 A | 1/1997 | Brauker et al. |
| 5,593,852 A | 1/1997 | Heller et al. |
| 5,624,537 A | 4/1997 | Turner et al. |
| 5,628,890 A | 5/1997 | Carter et al. |
| 5,640,954 A | 6/1997 | Pfeiffer |
| 5,653,756 A | 8/1997 | Clarke et al. |
| 5,653,863 A | 8/1997 | Genshaw et al. |
| 5,658,330 A | 8/1997 | Carlisle et al. |
| 5,660,163 A | 8/1997 | Schulman et al. |
| 5,683,562 A | 11/1997 | Schaffar et al. |
| 5,686,829 A | 11/1997 | Girault |
| 5,695,623 A | 12/1997 | Michel et al. |
| 5,704,354 A | 1/1998 | Preidel et al. |
| 5,706,807 A | 1/1998 | Picha |
| 5,711,861 A | 1/1998 | Ward et al. |
| 5,713,888 A | 2/1998 | Neuenfeldt et al. |
| 5,733,336 A | 3/1998 | Neuenfeldt et al. |
| 5,741,319 A | 4/1998 | Woloszko et al. |
| 5,741,330 A | 4/1998 | Brauker et al. |
| 5,743,262 A | 4/1998 | Lepper, Jr. et al. |
| 5,756,632 A | 5/1998 | Ward et al. |
| 5,776,324 A | 7/1998 | Usala |
| 5,777,060 A | 7/1998 | Van Antwerp |
| 5,779,665 A | 7/1998 | Mastrototaro et al. |
| 5,782,912 A | 7/1998 | Brauker et al. |
| 5,783,054 A | 7/1998 | Raguse et al. |
| 5,787,900 A | 8/1998 | Butler et al. |
| 5,791,344 A | 8/1998 | Schulman et al. |
| 5,795,774 A | 8/1998 | Matsumoto et al. |
| 5,798,065 A | 8/1998 | Picha |
| 5,800,420 A | 9/1998 | Gross |
| 5,800,529 A | 9/1998 | Brauker et al. |
| 5,804,048 A | 9/1998 | Wong et al. |
| 5,807,375 A | 9/1998 | Gross et al. |
| 5,807,406 A | 9/1998 | Brauker et al. |
| 5,811,487 A | 9/1998 | Schulz, Jr. et al. |
| 5,820,622 A | 10/1998 | Gross et al. |
| 5,833,603 A | 11/1998 | Kovacs et al. |
| 5,837,728 A | 11/1998 | Purcell |
| 5,840,240 A | 11/1998 | Stenoien et al. |
| 5,851,197 A | 12/1998 | Marano et al. |
| 5,861,019 A | 1/1999 | Sun et al. |
| 5,871,514 A | 2/1999 | Wiklund et al. |
| 5,882,354 A | 3/1999 | Brauker et al. |
| 5,882,494 A | 3/1999 | Van Antwerp |
| 5,897,578 A | 4/1999 | Wiklund et al. |
| 5,904,708 A | 5/1999 | Goedeke |
| 5,906,817 A | 5/1999 | Moullier et al. |
| 5,910,554 A | 6/1999 | Kempe et al. |
| 5,913,998 A | 6/1999 | Butler et al. |
| 5,914,026 A | 6/1999 | Blubaugh, Jr. et al. |
| 5,917,346 A | 6/1999 | Gord |
| 5,919,215 A | 7/1999 | Wiklund et al. |
| 5,931,814 A | 8/1999 | Alex et al. |
| 5,944,661 A | 8/1999 | Swette et al. |
| 5,957,854 A | 9/1999 | Besson et al. |
| 5,957,903 A | 9/1999 | Mirzaee et al. |
| 5,961,451 A | 10/1999 | Reber et al. |
| 5,964,261 A | 10/1999 | Neuenfeldt et al. |
| 5,964,745 A | 10/1999 | Lyles et al. |
| 5,964,804 A | 10/1999 | Brauker et al. |
| 5,964,993 A | 10/1999 | Blubaugh et al. |
| 5,965,380 A | 10/1999 | Heller et al. |
| 5,967,986 A | 10/1999 | Cimochowski et al. |
| 5,976,085 A | 11/1999 | Kimball et al. |
| 5,985,129 A | 11/1999 | Gough et al. |
| 5,999,848 A | 12/1999 | Gord et al. |
| 6,001,067 A | 12/1999 | Shults et al. |
| 6,001,471 A | 12/1999 | Bries et al. |
| 6,011,984 A | 1/2000 | Van Antwerp et al. |
| 6,013,113 A | 1/2000 | Mika |
| 6,016,448 A | 1/2000 | Busacker et al. |
| 6,049,727 A | 4/2000 | Crothall |
| 6,059,946 A | 5/2000 | Yukawa et al. |
| 6,060,640 A | 5/2000 | Pauley et al. |
| 6,063,637 A | 5/2000 | Arnold et al. |
| 6,066,083 A | 5/2000 | Slater et al. |
| 6,081,736 A | 6/2000 | Colvin et al. |
| 6,083,710 A | 7/2000 | Heller et al. |
| 6,088,608 A | 7/2000 | Schulman et al. |
| 6,091,975 A | 7/2000 | Daddona et al. |
| 6,093,172 A | 7/2000 | Funderburk et al. |
| 6,103,033 A | 8/2000 | Say et al. |
| 6,115,634 A | 9/2000 | Donders et al. |
| 6,117,290 A | 9/2000 | Say et al. |
| 6,119,028 A | 9/2000 | Schulman et al. |
| 6,121,009 A | 9/2000 | Heller et al. |
| 6,122,536 A | 9/2000 | Sun et al. |
| 6,134,461 A | 10/2000 | Say et al. |
| 6,135,978 A | 10/2000 | Houben et al. |
| 6,144,869 A | 11/2000 | Berner et al. |
| 6,144,871 A | 11/2000 | Saito et al. |
| 6,157,880 A | 12/2000 | Hauser et al. |
| 6,162,611 A | 12/2000 | Heller et al. |
| 6,167,614 B1 | 1/2001 | Tuttle et al. |
| 6,175,752 B1 | 1/2001 | Say et al. |
| 6,180,416 B1 | 1/2001 | Kurnik et al. |
| 6,187,062 B1 | 2/2001 | Oweis et al. |
| 6,189,536 B1 | 2/2001 | Martinez et al. |
| 6,200,772 B1 | 3/2001 | Vadgama et al. |
| 6,201,980 B1 | 3/2001 | Darrow et al. |
| 6,206,856 B1 | 3/2001 | Mahurkar |
| 6,208,894 B1 | 3/2001 | Schulman et al. |
| 6,212,416 B1 | 4/2001 | Ward et al. |
| 6,214,185 B1 | 4/2001 | Offenbacher et al. |
| 6,223,080 B1 | 4/2001 | Thompson |
| 6,223,083 B1 | 4/2001 | Rosar |
| 6,230,059 B1 | 5/2001 | Duffin |
| 6,231,879 B1 | 5/2001 | Li et al. |
| 6,233,471 B1 | 5/2001 | Berner et al. |
| 6,241,863 B1 | 6/2001 | Monbouquette |
| 6,248,067 B1 | 6/2001 | Causey, III et al. |
| 6,254,586 B1 | 7/2001 | Mann et al. |

(56) References Cited

U.S. PATENT DOCUMENTS

| | | |
|---|---|---|
| 6,256,522 B1 | 7/2001 | Schultz |
| 6,259,937 B1 | 7/2001 | Schulman et al. |
| 6,268,161 B1 | 7/2001 | Han et al. |
| 6,272,364 B1 | 8/2001 | Kurnik |
| 6,272,382 B1 | 8/2001 | Faltys et al. |
| 6,274,285 B1 | 8/2001 | Gries et al. |
| 6,275,717 B1 | 8/2001 | Gross et al. |
| 6,284,478 B1 | 9/2001 | Heller et al. |
| 6,285,897 B1 | 9/2001 | Kilcoyne et al. |
| 6,293,925 B1 | 9/2001 | Safabash et al. |
| 6,296,615 B1 | 10/2001 | Brockway et al. |
| 6,299,578 B1 | 10/2001 | Kurnik et al. |
| 6,300,002 B1 | 10/2001 | Webb et al. |
| 6,309,351 B1 | 10/2001 | Kurnik et al. |
| 6,309,384 B1 | 10/2001 | Harrington et al. |
| 6,325,978 B1 | 12/2001 | Labuda et al. |
| 6,325,979 B1 | 12/2001 | Hahn et al. |
| 6,326,160 B1 | 12/2001 | Dunn et al. |
| 6,329,161 B1 | 12/2001 | Heller et al. |
| 6,330,464 B1 | 12/2001 | Colvin, Jr. et al. |
| 6,343,225 B1 | 1/2002 | Clark, Jr. |
| 6,365,670 B1 | 4/2002 | Fry |
| 6,366,794 B1 | 4/2002 | Moussy et al. |
| 6,368,274 B1 | 4/2002 | Van Antwerp et al. |
| 6,372,244 B1 | 4/2002 | Antanavich et al. |
| 6,400,974 B1 | 6/2002 | Lesho |
| 6,405,066 B1 | 6/2002 | Essenpreis et al. |
| 6,406,066 B1 | 6/2002 | Uegane |
| 6,409,674 B1 | 6/2002 | Brockway et al. |
| 6,413,393 B1 | 7/2002 | Van Antwerp et al. |
| 6,424,847 B1 | 7/2002 | Mastrototaro et al. |
| 6,442,413 B1 | 8/2002 | Silver |
| 6,447,448 B1 | 9/2002 | Ishikawa et al. |
| 6,447,542 B1 | 9/2002 | Weadock |
| 6,454,710 B1 | 9/2002 | Ballerstadt et al. |
| 6,459,917 B1 | 10/2002 | Gowda et al. |
| 6,461,496 B1 | 10/2002 | Feldman et al. |
| 6,466,810 B1 | 10/2002 | Ward et al. |
| 6,471,689 B1 | 10/2002 | Joseph et al. |
| 6,475,750 B1 | 11/2002 | Han et al. |
| 6,477,392 B1 | 11/2002 | Honigs et al. |
| 6,477,395 B2 | 11/2002 | Schulman et al. |
| 6,481,440 B2 | 11/2002 | Gielen et al. |
| 6,484,046 B1 | 11/2002 | Say et al. |
| 6,497,729 B1 | 12/2002 | Moussy et al. |
| 6,498,043 B1 | 12/2002 | Schulman et al. |
| 6,514,718 B2 | 2/2003 | Heller et al. |
| 6,520,997 B1 | 2/2003 | Pekkarinen et al. |
| 6,527,729 B1 | 3/2003 | Turcott |
| 6,528,584 B2 | 3/2003 | Kennedy et al. |
| 6,537,318 B1 | 3/2003 | Ita et al. |
| 6,541,107 B1 | 4/2003 | Zhong et al. |
| 6,545,085 B2 | 4/2003 | Kilgour et al. |
| 6,546,268 B1 | 4/2003 | Ishikawa et al. |
| 6,547,839 B2 | 4/2003 | Zhang et al. |
| 6,551,496 B1 | 4/2003 | Moles et al. |
| 6,558,321 B1 | 5/2003 | Burd et al. |
| 6,560,471 B1 | 5/2003 | Heller et al. |
| 6,565,509 B1 | 5/2003 | Say et al. |
| 6,569,521 B1 | 5/2003 | Sheridan et al. |
| 6,579,498 B1 | 6/2003 | Eglise |
| 6,585,763 B1 | 7/2003 | Keilman et al. |
| 6,587,705 B1 | 7/2003 | Kim et al. |
| 6,591,125 B1 | 7/2003 | Buse et al. |
| 6,607,509 B2 | 8/2003 | Bobroff et al. |
| 6,613,379 B2 | 9/2003 | Ward et al. |
| 6,615,078 B1 | 9/2003 | Burson et al. |
| 6,618,934 B1 | 9/2003 | Feldman et al. |
| 6,642,015 B2 | 11/2003 | Vachon et al. |
| 6,645,181 B1 | 11/2003 | Lavi et al. |
| 6,648,821 B2 | 11/2003 | Lebel et al. |
| 6,654,625 B1 | 11/2003 | Say et al. |
| 6,666,821 B2 | 12/2003 | Keimel |
| 6,683,535 B1 | 1/2004 | Utke |
| 6,694,191 B2 | 2/2004 | Starkweather et al. |
| 6,695,860 B1 | 2/2004 | Ward et al. |
| 6,699,218 B2 | 3/2004 | Flaherty et al. |
| 6,702,857 B2 | 3/2004 | Brauker et al. |
| 6,702,972 B1 | 3/2004 | Markle |
| 6,721,587 B2 | 4/2004 | Gough |
| 6,731,976 B2 | 5/2004 | Penn et al. |
| 6,740,075 B2 | 5/2004 | Lebel et al. |
| 6,741,877 B1 | 5/2004 | Shults et al. |
| 6,773,565 B2 | 8/2004 | Kunimoto et al. |
| 6,793,632 B2 | 9/2004 | Sohrab |
| 6,793,802 B2 | 9/2004 | Lee et al. |
| 6,804,544 B2 | 10/2004 | van Antwerp et al. |
| 6,810,290 B2 | 10/2004 | Lebel et al. |
| 6,862,465 B2 | 3/2005 | Shults et al. |
| 6,895,263 B2 | 5/2005 | Shin et al. |
| 6,931,327 B2 | 8/2005 | Goode et al. |
| 6,936,006 B2 | 8/2005 | Sabra |
| 6,952,604 B2 | 10/2005 | DeNuzzio et al. |
| 6,991,643 B2 | 1/2006 | Saadat |
| 7,058,437 B2 | 6/2006 | Buse et al. |
| 7,074,307 B2 | 7/2006 | Simpson et al. |
| 7,081,195 B2 | 7/2006 | Simpson et al. |
| 7,108,778 B2 | 9/2006 | Simpson et al. |
| 7,110,803 B2 | 9/2006 | Shults et al. |
| 7,134,999 B2 | 11/2006 | Brauker et al. |
| 7,136,689 B2 | 11/2006 | Shults et al. |
| 7,153,265 B2 | 12/2006 | Vachon |
| 7,166,074 B2 | 1/2007 | Reghabi et al. |
| 7,169,289 B2 | 1/2007 | Schulein et al. |
| 7,192,450 B2 | 3/2007 | Brauker et al. |
| 7,225,535 B2 | 6/2007 | Feldman et al. |
| 7,329,239 B2 | 2/2008 | Safabash et al. |
| 7,344,499 B1 | 3/2008 | Prausnitz et al. |
| 7,364,592 B2 | 4/2008 | Carr-Brendel et al. |
| 7,404,819 B1 | 7/2008 | Darios et al. |
| 7,417,164 B2 | 8/2008 | Suri |
| 7,426,408 B2 | 9/2008 | DeNuzzio et al. |
| 7,632,228 B2 | 12/2009 | Brauker et al. |
| 7,657,297 B2 | 2/2010 | Simpson et al. |
| 2002/0022883 A1 | 2/2002 | Burg |
| 2002/0042090 A1 | 4/2002 | Heller et al. |
| 2002/0055673 A1 | 5/2002 | Van Antwerp et al. |
| 2002/0151796 A1 | 10/2002 | Koulik |
| 2002/0151816 A1 | 10/2002 | Rich et al. |
| 2002/0169369 A1 | 11/2002 | Ward et al. |
| 2002/0182241 A1 | 12/2002 | Borenstein et al. |
| 2002/0188185 A1 | 12/2002 | Sohrab |
| 2002/0193885 A1 | 12/2002 | Legeay et al. |
| 2003/0006669 A1 | 1/2003 | Pei et al. |
| 2003/0023317 A1 | 1/2003 | Brauker et al. |
| 2003/0032874 A1 | 2/2003 | Rhodes et al. |
| 2003/0036803 A1 | 2/2003 | McGhan et al. |
| 2003/0059631 A1 | 3/2003 | Al-Lamee |
| 2003/0070548 A1 | 4/2003 | Clausen |
| 2003/0076082 A1 | 4/2003 | Morgan et al. |
| 2003/0078481 A1 | 4/2003 | McIvor et al. |
| 2003/0078560 A1 | 4/2003 | Miller et al. |
| 2003/0091433 A1 | 5/2003 | Tam et al. |
| 2003/0125613 A1 | 7/2003 | Enegren et al. |
| 2003/0130616 A1 | 7/2003 | Steil et al. |
| 2003/0181794 A1 | 9/2003 | Rini et al. |
| 2003/0188427 A1 | 10/2003 | Say et al. |
| 2003/0199744 A1 | 10/2003 | Buse et al. |
| 2003/0199745 A1 | 10/2003 | Burson et al. |
| 2003/0217966 A1 | 11/2003 | Tapsak et al. |
| 2003/0225361 A1 | 12/2003 | Sabra |
| 2003/0235817 A1 | 12/2003 | Bartkowiak et al. |
| 2004/0010207 A1 | 1/2004 | Flaherty et al. |
| 2004/0011671 A1 | 1/2004 | Shults et al. |
| 2004/0015063 A1 | 1/2004 | DeNuzzio et al. |
| 2004/0015134 A1 | 1/2004 | Lavi et al. |
| 2004/0030285 A1 | 2/2004 | Lavi et al. |
| 2004/0030294 A1 | 2/2004 | Mahurkar |
| 2004/0039406 A1 | 2/2004 | Jessen |
| 2004/0045879 A1 | 3/2004 | Shults et al. |
| 2004/0068230 A1 | 4/2004 | Estes et al. |
| 2004/0087671 A1 | 5/2004 | Tamada et al. |
| 2004/0106857 A1 | 6/2004 | Gough |
| 2004/0186362 A1 | 9/2004 | Brauker et al. |

(56) References Cited

U.S. PATENT DOCUMENTS

| | | |
|---|---|---|
| 2004/0186365 A1 | 9/2004 | Jin et al. |
| 2004/0199059 A1 | 10/2004 | Brauker et al. |
| 2004/0219664 A1 | 11/2004 | Heller et al. |
| 2005/0008671 A1 | 1/2005 | Van Antwerp |
| 2005/0027180 A1 | 2/2005 | Goode et al. |
| 2005/0027181 A1 | 2/2005 | Goode et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0043598 A1 | 2/2005 | Goode et al. |
| 2005/0051427 A1 | 3/2005 | Brauker et al. |
| 2005/0054909 A1 | 3/2005 | Petisce et al. |
| 2005/0056552 A1 | 3/2005 | Simpson et al. |
| 2005/0059871 A1 | 3/2005 | Gough et al. |
| 2005/0090607 A1 | 4/2005 | Tapsak et al. |
| 2005/0096519 A1 | 5/2005 | DeNuzzio et al. |
| 2005/0112169 A1 | 5/2005 | Brauker et al. |
| 2005/0121322 A1 | 6/2005 | Say |
| 2005/0192557 A1 | 9/2005 | Brauker et al. |
| 2005/0211571 A1 | 9/2005 | Schulein et al. |
| 2005/0242479 A1 | 11/2005 | Petisce et al. |
| 2005/0245795 A1 | 11/2005 | Goode et al. |
| 2005/0245799 A1 | 11/2005 | Brauker et al. |
| 2005/0251083 A1 | 11/2005 | Carr-Brendel et al. |
| 2006/0015020 A1 | 1/2006 | Neale et al. |
| 2006/0200022 A1 | 9/2006 | Brauker et al. |
| 2006/0211921 A1 | 9/2006 | Brauker et al. |
| 2006/0224108 A1 | 10/2006 | Brauker et al. |
| 2006/0257995 A1 | 11/2006 | Simpson et al. |
| 2006/0257996 A1 | 11/2006 | Simpson et al. |
| 2006/0263763 A1 | 11/2006 | Simpson et al. |
| 2006/0270922 A1 | 11/2006 | Brauker et al. |
| 2006/0270923 A1 | 11/2006 | Brauker et al. |
| 2006/0281985 A1 | 12/2006 | Ward et al. |
| 2007/0027370 A1 | 2/2007 | Brauker et al. |
| 2007/0032718 A1 | 2/2007 | Shults et al. |
| 2007/0045902 A1 | 3/2007 | Brauker et al. |
| 2007/0235331 A1 | 10/2007 | Simpson et al. |
| 2008/0045824 A1 | 2/2008 | Tapsak et al. |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0305009 A1 | 12/2008 | Gamsey et al. |
| 2008/0305506 A1 | 12/2008 | Suri |
| 2009/0018418 A1 | 1/2009 | Markle et al. |
| 2009/0018426 A1 | 1/2009 | Markle et al. |
| 2009/0030297 A1 | 1/2009 | Miller et al. |
| 2009/0036763 A1 | 2/2009 | Brauker et al. |
| 2009/0061528 A1 | 3/2009 | Suri |
| 2009/0062633 A1 | 3/2009 | Brauker et al. |
| 2009/0081803 A1 | 3/2009 | Gamsey et al. |
| 2009/0177143 A1 | 7/2009 | Markle et al. |
| 2009/0264719 A1 | 10/2009 | Markle et al. |
| 2010/0160760 A1 | 6/2010 | Shults et al. |
| 2010/0256779 A1 | 10/2010 | Brauker et al. |

FOREIGN PATENT DOCUMENTS

| | | |
|---|---|---|
| EP | 0 127 958 | 12/1984 |
| EP | 0 320 109 | 6/1989 |
| EP | 0 353 328 | 2/1990 |
| EP | 0 390 390 | 10/1990 |
| EP | 0 534 074 | 3/1993 |
| EP | 0 535 898 | 4/1993 |
| EP | 0 563 795 | 10/1993 |
| EP | 0 776 628 | 6/1997 |
| EP | 0 817 809 | 1/1998 |
| EP | 0 885 932 | 12/1998 |
| FR | 2656423 | 6/1991 |
| FR | 2760962 | 9/1998 |
| GB | 1 442 303 | 7/1976 |
| GB | 2149918 | 6/1985 |
| JP | 62083849 | 4/1997 |
| WO | WO 89-02720 | 4/1989 |
| WO | WO 90-00738 | 1/1990 |
| WO | WO 92-07525 | 5/1992 |
| WO | WO 92-13271 | 8/1992 |
| WO | WO 93-14693 | 8/1993 |
| WO | WO 93-19701 | 10/1993 |
| WO | WO 94-22367 | 10/1994 |
| WO | WO 95-07109 | 3/1995 |
| WO | WO 96-01611 | 1/1996 |
| WO | WO 96-14026 | 5/1996 |
| WO | WO 96-25089 | 8/1996 |
| WO | WO 96-30431 | 10/1996 |
| WO | WO 96-32076 | 10/1996 |
| WO | WO 96-36296 | 11/1996 |
| WO | WO 97-01986 | 1/1997 |
| WO | WO 97-43633 | 11/1997 |
| WO | WO 98-24358 | 6/1998 |
| WO | WO 98-38906 | 9/1998 |
| WO | WO 99-56613 | 4/1999 |
| WO | WO 00-13003 | 3/2000 |
| WO | WO 00-19887 | 4/2000 |
| WO | WO 00-32098 | 6/2000 |
| WO | WO 00-33065 | 6/2000 |
| WO | WO 00-59373 | 10/2000 |
| WO | WO 00-74753 | 12/2000 |
| WO | WO 01-12158 | 2/2001 |
| WO | WO 01-20019 | 3/2001 |
| WO | WO 01-20334 | 3/2001 |
| WO | WO 01-34243 | 5/2001 |
| WO | WO 01-43660 | 6/2001 |
| WO | WO 01-88524 | 11/2001 |
| WO | WO 01-88534 | 11/2001 |
| WO | WO 02-053764 | 7/2002 |
| WO | WO 03-101862 | 12/2003 |

OTHER PUBLICATIONS

Abe et al., 1992. Characterization of glucose microsensors for intracellular measurements. Analytical Chemistry 64(18):2160-2163.

Abel et al., 1984. Experience with an implantable glucose sensor as a prerequisite of an artificial beta cell. Biomed. Biochim. Acta 43(5):577-584.

Abel et al., 2002. Biosensors for in vivo glucose measurement: can we cross the experimental stage. Biosensors & Bioelectronics 17:1059-1070.

Alcock & Turner, 1994. Continuous Analyte Monitoring to Aid Clinical Practice. IEEE Transactions on Engineering in Med. & Biol. Mag. 13:319-325.

Amato et al., Jun. 1989. Experience with the Polytetrafluoroethylene Surgical Membrane for Pericardial Closure in Operations for Congenital Cardiac Defects. J Thoracic Cardiovascular Surgery 97(6):929-934.

American Heritage Dictionary, 4th Edition. 2000. Houghton Mifflin Company, p. 82.

Answers.com. "xenogenic." The American Heritage Stedman's Medical Dictionary, Houghton Mifflin Company, 2002. Answers.com, downloaded Nov. 7, 2006 from http://www.answers.com-topic-xenogenic.

Armour et al., Dec. 1990. Application of Chronic Intravascular Blood Glucose Sensor in Dogs. Diabetes 39:1519-1526.

Atanasov et al., 1994. Biosensor for continuous glucose monitoring. Biotechnology and Bioengineering 43:262-266.

Atanasov et al., 1997. Implantation of a refillable glucose monitoring-telemetry device. Biosensors & Bioelectronics 12:669-680.

Aussedat et al., 1997. A user-friendly method for calibrating a subcutaneous glucose sensor-based hypoglycaemic alarm. Biosensors & Bioelectronics 12(11):1061-1071.

Baker et al., 1993. Dynamic concentration challenges for biosensor characterization. Biosensors & Bioelectronics 8:433-441.

Bani Amer, M. M. 2002. An accurate amperometric glucose sensor based glucometer with eliminated cross-sensitivity. J Medical Engineering Technology 26(5):208-213.

(56) References Cited

OTHER PUBLICATIONS

Beach et al., 1999. Subminiature implantable potentiostat and modified commercial elemetry device for remote glucose monitoring. IEEE Transactions on Instrumentation and Measurement 48(6):1239-1245.
Bellucci et al., Jan. 1986. Electrochemical behaviour of graphite-epoxy composite materials (GECM) in aqueous salt solutions. Journal of Applied Electrochemistry 16(1): 15-22.
Bessman et al., 1973. Progress toward a glucose sensor for the artificial pancreas. Proceedings of a Workshop on Ion-Selective Microelectrodes, Jun. 4-5, 1973, Boston, MA, pp. 189-197.
Bindra et al., 1989. Pulsed amperometric detection of glucose in biological fluids at a surface-modified gold electrode. Analytical Chemistry 61:2566-2570.
Bindra et al., 1991. Design and In Vitro Studies of a Needle-Type Glucose Sensor for Subcutaneous Monitoring. Analytical Chemistry 63:1692-1696.
Bisenberger et al., 1995. A triple-step potential waveform a enzyme multisensors with thick-film gold electrodes for detection of glucose and sucrose. Sensors and Actuators B 28:181-189.
Bland et al., 1990. A note on the use of the intraclass correlation coefficient in the evaluation of agreement between two methods of meaurement. Comput. Biol. Med. 20(5):337-340.
Bobbioni-Harsch et al., 1993. Lifespan of subcutaneous glucose sensors and their performances during dynamic glycaemia changes in rats. J. Biomedical Engineering 15:457-463.
Bode et al., 1999. Continuous glucose monitoring used to adjust diabetes therapy improves glycosylated hemoglobin: A pilot study. Diabetes Research and Clinical Practice 46:183-190.
Bode et al., 2000. Using the continuous glocuse monitoring system to improve the management of type 1 diabetes. Diabetes Technology & Therapeutics 2(Suppl 1):S43-S48.
Bode, B. W. 2000. Clinical utility of the continuous glucose monitoring system. Diabetes Technology & Therapeutics 2(Suppl 1):S35-S41.
Boland et al., 2001. Limitations of conventional methods of self-monitoring of blood glucose. Diabetes Care 24(11): 1858-1862.
Bott, A. W. 1997. A Comparison of Cylic Voltammetry and Cyclic Staircase Voltammetry. Curent Separations 16(1):23-26.
Bowman, L.; Meindl, J. D. 1986. The packaging of implantable integrated sensors. IEEE Transactions on Biomedical Engineering (BME) 33(2):248-255.
Brauker et al., 1995. Neovascularization of synthetic membranes directed by membrane Microarchitecture. J. Biomedical Materials Research 29:1517-1524.
Brauker et al., 1998. Sustained expression of high levels of human factor IX from human cells implanted within an immunoisolation device into athymic rodents. Human Gene Therapy 9:879-888.
Braucker et al., 2001. Unraveling Mysteries at the Biointerface: Molecular Mediator of Inhibition of Blood vessel Formation in the Foreign Body Capsule Revealed. Surfacts Biomaterials 6. 1-5.
Brauker et al., Jun. 27, 1996. Local Inflammatory Response Around Diffusion Chambers Containing Xenografts. Transplantation 61(12):1671-1677.
Brauker J., 1992. Abstract:. Neovascularization of Cell Transplantation Devices: Membrane Architecture—Driven an Implanted Tissue—Driven Vascularization. Baxter Healthcare Corp. Abstract from the 4th World Biomaterials Congress, Berlin.
Bremer et al., 2001. Benchmark data from the literature for evaluation of new glucose sensing technologies. Diabetes Technology & Therapeutics 3(3):409-418.
Brooks et al., 1987-88. Development of an on-line glucose sensor for fermentation monitoring. Biosensors 3:45-56.
Bruckel et al., 1989. In vivo measurement of subcutaneous glucose concentrations with an enzymatic glucose sensor and a wick method. Klin Wochenschr 67:491-495.
Brunner et al., 1998. Validation of home blood glucose meters with respect to clinical and analytical approaches. Diabetes Care 21(4):585-590.
Cai et al., 2004. A wireless, remote query glucose biosensor based on a pH-sensitive polymer. Analytical Chemistry 76(4):4038-4043.
Campanella et al., 1993. Biosensor for direct determination of glucose and lactate in undiluted biological fluids. Biosensors & Bioelectronics 8:307-314.
Candas et al., 1994. An adaptive plasma glucose controller based on a nonlinear insulin-glucose model. IEEE Transactions on Biomedical Engineering 41(2): 116-124.
Cass et al., 1984. Ferrocene-mediated enzyme electrodes for amperometric determination of glucose. Analytical Chemistry 36:667-671.
Cassidy et al., Apr. 1993. Novel electrochemical device for detection of cholesterol or glucose. Analyst 118:415-418.
Chase et al., 2001. Continuous subcutaneous glucose monitoring in childen with type 1 diabetes. Pediatrics 107:222-226.
Chatterjee et al., 1997. Poly(ether Urethane) and poly(ether urethane urea) membranes with high H2S-CH4 selectivity. Journal of Membrane Science 135:99-106.
Ciba® Irgacure® 2959 Photoinitiator, Product Description, Ciba Specialty Chemicals Inc., Basel, Switzerland, Apr. 2, 1998.
Claremont et al., 1986. Subcutaneous implantation of a ferrocene-mediated glucose sensor in pigs. Diabetologia 29:817-821.
Claremont et al., Jul. 1986. Potentially-implantable, ferrocene-mediated glucose sensor. J. Biomedical Engineering 8:272-274.
Clark et al., 1981. One-minute electrochemical enzymic assay for cholesterol in biological materials. Clinical Chemistry 27(12):1978-1982.
Clark et al,, 1987. Configurational cyclic voltarmmetry: increasing the specificity and reliability of implanted electrodes. IEEE-Ninth Annual Conference of the Engineering in Medicine and Biology Society, pp. 0782-0783.
Clark et al., 1988. Long-term stability of electroenzymatic glucose sensors implanted in mice. Transactions of the American Society of Artificial Internal Organs 34:259-265.
Colangelo et al., 1967. Corrosion rate measurements in vivo. Journal of Biomedical Materials Research 1:405-414.
Colowick et al., 1976. Methods in Enzymology, vol. XLIV, Immobilized Enzymes. New York: Academic Press.
Copeland et al., Jun. 2001. Synthetic Membrane Neo-Pericardium Facilitates Total Artificial Heart Explantation, J Heart and Lung Transplantation 20(6): 654-656.
Cox et al., 1985. Accuracy of perceiving blood glucose in IDDM. Diabetes Care 8(6):529-536.
Csoregi et al., 1994. Design, characterization, and one-point in vivo calibration of a subcutaneously implanted glucose electrode. Analytical Chemistry 66(19):3131-3138.
Dai et al., 1999. Hydrogel Membranes with Mesh Size Asymmetry Based on the Gradient Crosslink of Poly(vinyl alcohol). Journal of Membrane Science 156:67-79.
Danielsson et al., 1988. Enzyme thermistors. Methods in Enzymology 137:181-197.
D'Arrigo et al., 2003. Porous-Si based bioreactors for glucose monitoring and drugs production. Proc. of SPIE 4982:178-184.
Davis, et al., Sep. 1992. Polymer membranes in clinical sensor applicaions. I. An overview of membrane function. Biomaterials 13(14):971-978.
Davis et al., Sep. 1983. Bioelectrochemical fuel cell and sensor based on a quinoprotein, alcohol dehydrogenase. Enzyme Microb. Technol. 5:383-388
Direct 30-30® meter (Markwell Medical) (Catalog), 1990.
Dixon et al., 2002, Characterization in vitro and in vivo of the oxygen dependence of an enzyme-polymer biosensor for monitoring brain glucose. Journal of Neuroscience Methods 119:135-142.
DuPont[1] Dimension AR® (Catalog), 1998.
Durliat et al., 1976. Spectrophotometric and electrochemical determinations of L(+)-lactate in blood by use of lactate dehydrogenase from yeast. Clinical Chemistry 22(11): 1802-1805.
El Degheidy et al., 1986. Optimization of an implantable coated wire glucose sensor. J. Biomed Eng. 8: 121-129.
El-Sa'ad et al., 1990. Moisture Absorption by Epoxy Resins: the Reverse Thermal Effect. Journal of Materials Science 25:3577-3582.

(56) References Cited

OTHER PUBLICATIONS

Ernst et al., 2002. Reliable glucose monitoring through the use of microsystem technology, Analytical & Bioanalytical Chemistry 373:758-761.
Fare et al., 1998. Functional characterization of a conducting polymer-based immunoassay system. Biosensors & Bioelectronics 13(3-4):459-470.
Feldman et al., 2003. A continuous glucose sensor based on wired enzyme technology—results from a 3-day trial in patients with type 1 diabetes. Diabetes Technology & Therapeutics 5(5):769-779.
Fischer et al., 1987. Assessment of subcutaneous glucose concentration: validation of the wick technique as a reference for implanted electrochemical sensors in normal and diabetic dogs. Diabetologia 30:940-945.
Fischer et al., 1989. Oxygen Tensions at the Subcutaneous Implantation Site of Glucose Sensors. Biomed. Biochem 11-12:965-972.
Fischer et al., 1995. Abstract: Hypoglycaemia—warning by means of subcutaneous electrochemical glucose sensors: an animal study. Horm. Metab. Res. 27-53.
Freedman et al., 1991. Statistics, Second Edition, W.W. Norton & Company, p. 74.
Frohnauer et al., 2001. Graphical human insulin time-activity profiles using standardized definitions. Diabetes Technology & Therapeutics 3(3):419-429.
Frost et al., 2002. Implantable chemical sensors for real-time clinical monitoring: Progress and challenges. Current Opinion in Chemical Biology 6:633-641.
Gao et al., 1989. Determination of Interfacial parameters of cellulose acetate membrane materials by HPLC. J. Liquid Chromatography 12(11):2083-2092.
Garg et al., 2004. Improved Glucose Excursions Using an implantable Real-Time continuous Glucose Sensor in Adults with Type I Diabetes. Diabetes Care. 27:734-738.
Geller et al., 1997. Use of an immunoisolation device for cell transplantation and tumor immunotherapy. Annals of the New York Academy of Science. 831:438-451.
Gerritsen et al., 1999. Performance of subcutaneously implanted glucose sensors for continuous monitoring. The Netherlands Journal of Medicine 54:167-179.
Gerritsen et al., 2001. Influence of inflammatory cells and serum on the performance of implantable glucose sensors. Journal of Biomedical Materials Research 54:69-75.
Gerritsen, M. 2000. Problems associated with subcutaneously implanted glucose sensors. Diabetes Care 23(2):143-145.
Gilligan et al., 1994. Evaluation of a subcutaneous glucose sensor out to 3 months in a dog model. Diabetes Care 17(8):882-887.
Gilligan et al., 2004. Feasibility of continuous long-term glucose monitoring from a subcutaneous glucose sensor in humans. Diabetes Technology & Therapeutics 6:378-386.
Godsland et al., 2001. Maximizing the Success Rate of Minimal Model Insulin Sensitivity Measurement in Humans: The Importance of Basal Glucose Levels. The Biochemical Society and the Medical Research Society, pp. 1-9.
Gore Preclude® Pericardial Membrane Brochure, Jun. 2009, W.L. Gore & Associates, Inc., Flagstaff, AZ 86004.
Gough et al., 2000. Immobilized glucose oxidase in implantable glucose sensor technology. Diabetes Technolog & Therapeutics 2(3):377-380.
Gregg et al., 1990. Cross-Linked Redox Gels Containing Glucose Oxidase for Amperometric Biosensor Applications. Analytical Chemistry 62:258-263.
Gross et al., 2000. Efficacy and reliability of the continuous glucose monitoring system. Diabetes Technology & Therapeutics 2(Suppl 1):S19-S26.
Gross et al., 2000. Performance evaluation of the MiniMed® continuous glucose monitoring system during patient home use. Diabetes Technology & Therapeutics 2(1):49-56 (2000) & 3(1):130-131 (2001).
Guo et al., 1998. Modification of cellulose acetate ultrafiltration membrane by gamma ray radiation. Shuichuli Jishi Bianji Weiyuanhui 23(6):315-318 (Abstract).
Hall et al., 1998. Electrochemical oxidation of hydrogen peroxide at platinum electrodes. Part II: Effect of potential. Electrochimica Acta 43(14-15):2015-2024.
Hall et al., 1998. Electrochemical oxidation of hydrogen peroxide at platinum electrodes Part I: An adsorption-controlled mechanism. Electrochimica Acta 43(5-6):579-288.
Hall et al., 1999. Electrochemical oxidation of hydrogen peroxide at platinum electrodes. Part III: Effect of temperature. Electrochimica Acta 44:2455-2462.
Hall et al., 1999. Electrochemical oxidation of hydrogen peroxide at platinum electrodes. Part IV: Phosphate buffer dependence. Electrochimica Acta 44:4573-4582.
Hall et al., 2000. Electrochemical oxidation of hydrogen peroxide at platinum electrodes. Part V: Inhibition by chloride. Electrochimica Acta 45:3573-3579.
Harada et al., Nov. 1988. Long-term Results of the Clinical Use of an Expanded Polytetrafluoroethylene Surgical Membrane as a Pericardial Substitute. J Thorac Cardiovascular Surgery 96(5): 811-815.
Harrison et al., 1988. Characterization of perfluorosulfonic acid polymer coated enzyme electrodes and a miniaturized integrated potentiostat for glucose analysis in whole blood. Analytical Chemistry 60:2002-2007.
Hashiguchi et al., 1994. Development of a miniaturized glucose monitoring system by combining a needle-type glucose sensor with microdialysis sampling method: Long-term subcutaneous tissue glucose monitoring in ambulatory diabetic patients. Diabetes Care 17(5): 387-396.
Heller, 1990. Electrical wiring of redox enzymes. Acc. Chem. Res. 23:128-134.
Heller, A. 1992. Electrical Connection of Enzyme Redox Centers to Electrodes. J. Physical Chemistry 96:3579-3587.
Heller, A. 1999. Implanted electrochemical glucose sensors for the management of diabetes. Annu Rev Biomedical Engineering 1:153-175.
Heller, A. 2003. Plugging metal connectors into enzymes. Nature Biotechnology 21:631-632.
Heydorn et al., Aug. 1987. A New Look at Pericardial Substitutes. J Thorac Cardiovascular Surgery 94(2): 291-296.
Hicks, 1985. In Situ Monitoring. Clinical Chemistry 31(12):1931-1935.
Hitchman, M. L. 1978. Measurement of Dissolved Oxygen. In Elving et al. (Eds.). Chemical Analysis vol. 49, Chap. 3, pp. 34-49, 59-123. New York: John Wiley & Sons.
Hoel, Paul G. 1976. Elementary Statistics, Fourth Edition. John Wiley & Sons, Inc.. pp. 113-114.
Hrapovic et al., 2003. Picoamperometric detection of glucose at ultrasmall platinum-based biosensors: preparation and characterization. Analytical Chemistry 75:3308-3315.
Hu, et al., 1993. A needle-type enzyme-based lactate sensor for in vivo monitoring. Analytica Chimica Acta 281:503-511.
Huang et al., Aug. 1975. Electrochemical Generation of Oxygen. 1: The Effects of Anions and Cations on Hydrogen Chemisorption and Anodic Oxide Film Formation on Platinum Electrode. 2: The Effects of Anions and Cations on Oxygen Generation on Platinum Electrode. U.S. Department of Commerce National Technical Information Service N7625362.
Huang et al., Sep. 1997. A 0.5mW Passive Telemetry IC for Biomedical Applications. Proceedings of the 23rd European Solid-State Circuits Conference (ESSCIRC '97), Southampton, UK, pp. 172-175.
Hunter et al., 2000. Minimally Invasive Glucose Sensor and Insulin Delivery System. MIT Home Automation and Healthcare Consortium, Progress Report No. 25.
Ishikawa et al., 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and its Complications 12:295-301.

(56) References Cited

OTHER PUBLICATIONS

Jaffari et al., 1995. Recent advances in amperometric glucose biosensors for in vivo monitoring. Physiol. Meas. 16: 1-15.
Jensen et al., 1997. Fast wave forms for pulsed electrochemical detection of glucose by incorporation of reductive desorption of oxidation products. Analytical Chemistry 69(9):1776-1781.
Jeutter, D.C. 1982. A transcutaneous implanted battery recharging an biotelemeter power switching system. IEEE Transactions on Biomedical Engineering 29:314-321.
Jobst et al., 1996. Thin-Film Microbiosensors for Glucose-Lactate Monitoring. Analytical Chemistry 68(18): 3173-3179.
Johnson 1991. Reproducible electrodeposition of biomolecules for the fabrication of miniature electroenzymatic biosensors. Sensors and Actuators B 5:85-89.
Johnson et al., 1992. In vivo evaluation of an electroenzymatic glucose sensor implanted in subcutaneous tissue, Biosensors & Bioelectronics 7:709-714.
Johnson et al., 1997. Abstract: Neovascularization of cell transplantation devices: Role of membrane architecture and encapsulated tissue, Abstracts of Papers. Am. Chem. Soc. 214:305-PMSE.
Jovanovic, L. 2000. The role of continuous glucose monitoring in gestational diabetes mellitus. Diabetes Technology & Therapeutics 2(Suppl 1): S67-S71.
Kacaniklic et al., May-Jun. 1994. Amperometric Biosensors for Detection of L- and D-Amino Acids Based on Coimmobilized Peroxidase and L- and D-Amino Acid Oxidases in Carbon Paste Electrodes. Electroanalysis 6(5-6):381-390.
Kang et al., 2003. In vitro and short-term in vivo characteristics of a Kel-F thin film modified glucose sensor. Analytical Science 19:1481-1486.
Kargol et al., 2001. Studies on the structural properties of porous membranes: measurement of linear dimensions of solutes. Biophys. Chem. 91:263-271.
Karubeetal. 1993. Microbiosensors for acetylcholine and glucose. Biosensors & Bioelectronics 8:219-228.
Kaufman et al., 2001. A pilot study of the continuous glucose monitoring system. Diabetes Care 24(12):2030-2034.
Kaufman. 2000. Role of the continuous glucose monitoring system in pediatric patients. Diabetes Technology & Therapeutics 2(Supp 1):S49-S52.
Kawagoe et al., 1991. Enzyme-modified organic conducting salt microelectrode. Analytical Chemistry 63:2961-2965.
Keedyetal. 1991. Determination of urate in undiluted whole blood by enzyme electrode. Biosensors & Bioelectronics 6: 491-499.
Kerner et al., 1988. A potentially implantable enzyme electrode for amperometric measurement of glucose. Horm Metab Res Suppl. 20:8-13.
Kerner et al., 1993. The function of a hydrogen peroxide-detecting electroenzymatic glucose electrode is markedly impaired in human sub-cutaneous tissue and plasma. Biosensors & Bioelectronics 8:473-482.
Kiechle, F.L. 2001. The impact of continuous glucose monitoring on hospital point-of-care testing programs. Diabetes Technology & Therapeutics 3:647-649.
Ko, Wen H. 1985. Implantable Sensors for Closed-Loop Prosthetic Systems, Futura Pub. Co., Inc., Mt. Kisco, NY, Chapter 15, pp. 197-210.
Kondo et al., 1982. A miniature glucose sensor, implantable in the blood stream. Diabetes Care 5(3):218-221.
Koschinsky et al., 1988. New approach to technical and clinical evaluation of devices for self monitoring of blood glucose. Diabetes Care 11 (8):619-619.
Koschinsky et al., 2001. Sensors for glucose monitoring: Technical and clinical aspects. Diabetes Metab. Res. Rev. 17:113-123.
Kost et al., 1985. Glucose-sensitive membranes containing glucose oxidase: activity, swelling, and permeability studies. Journal of Biomedical Materials Research 19:1117-1133.
Koudelka et al., 1989. In vivo response of microfabricated glucose sensors to glycemia changes in normal rats. Biomed Biochim Acta 48(11-12):953-956.
Koudelka et al., 1991. In-vivo behaviour of hypodermically implanted microfabicated glucose sensors. Biosensors & Bioelectronics 6:31-36.
Kraver et al., 2001. A mixed-signal sensor interface microinstrument. Sensors and Actuators A 91:266-277.
Kruger et al., 2000. Psychological motivation and patient education: A role for continuous glucose monitoring. Diabetes Technology & Therapeutics 2(Suppl 1):S93-S97.
Kulys et al., 1994. Carbon-paste biosensors array for long-term glucose measurement. Biosensors & Beioelectronics 9:491-500.
Kunzler et al., 1993. Hydrogels based on hydrophilic side chain siloxanes. Poly Mat Sci and Eng 69:226-227.
Kunzler et al., Aug. 21, 1995. Contact lens materials. Chemistry & Industry. 651-655.
Ladd et al., 1996. Structure Determination by X-ray Crystallography, 3rd ed. Plenum, 1996, Ch. 1, pp. xxi-xxiv and pp. 1-58.
Lee et al., 1999. Effects of pore size, void volume, and pore connectivity on tissue responses. Society for Biomaterials 25th Annual Meeting, p. 171.
Lehmann et al., May 1994. Retrospective validation of a physiological model of glucose-insulin interaction in type 1 diabetes mellitus. Med. Eng. Phys. 16:193-202.
Leprince et al., Jan. 2001. Expanded Polytetrafluoroethylene Membranes to Wrap Surfaces of Circulatory Support Devices in Patients Undergoing Bridge to Heart Transplantation. European J Cardiothoracic Surgery 19:302-306.
Lerner et al., 1984. An implantable electrochemical glucose sensor. Ann. N. Y. Acad. Sci. 428:263-278.
Lewandowski et al., 1988. Evaluation of a miniature blood glucose sensor. Transactions of the American Society of Artificial Internal Organs 34:255-258.
Leypoldt et al., 1984. Model of a two-substrate enzyme electrode for glucose. Analytical Chemistry 56:2896-2904.
Linke et al., 1994. Amperometric biosensor for in vivo glucose sensing based on glucose oxidase immobilized in a redox hydrogel. Biosensors & Bioelectronics 9:151-158.
Loebe et al., 1993. Use of Polytetrafluoroethylene Surgical Membrane as a Pericardial Substitute. PTFE Membrane in Correction of Congenital Heart Defects—Texas Heart Institute Journal 20(3):213-217.
Loffler et al., 1995. Separation and determination of traces of ammonia in air by means of chromatomembrane cells. Fresenius J Analytical Chemistry 352:613-614.
Lowe, 1984. Biosensors. Trends in Biotechnology 2(3)59-65.
Lyman D. 1960. Polyurethanes. I. The Solution Polymerization of Diisocyanates with Ethylene Glycol. J. Polymer Sci XLV:49-59.
Madaras et al., 1996. Microfabricated amperometric creatine and creatinine biosensors. Analytica Chimica Acta 319:335-345.
Maidan et al., 1992. Elimination of Electrooxidizable Interferent-Produced Currents in Amperometric Biosensors. Analytical Chemistry 64:2889-2896.
Makale et al., 2003. Tissue window chamber system for validation of implanted oxygen sensors. Am. J. Physiol. Heart Circ. Physiol. 284:H2288-2294.
Malin et al., 1999, Noninvasive Prediction of Glucose by Near-Infrared Diffuse Reflectance Spectroscopy. Clinical Chemistry 45(9):1651-1658.
Maran et al., 2002. Continuous subcutaneous glucose monitoring in diabetic patients: A multicenter analysis. Diabetes Care 25 (2):347-352.
March, W. F. 2002. Dealing with the delay. Diabetes Technology & Therapeutics 4(1):49-50.
Marena et al., 1993. The artificial endocrine pancreas in clinical practice and research. Panminerva Medica 35(2):67-74.
Mascini et al., 1989. Glucose electrochemical probe with extended linearity for whole blood. J Pharm Biomed Anal 7(12):1507-1512.
Mastrototaro et al., 1991. An electroenzymatic glucose sensor fabricataed on a flexible substrate. Sensors and Actuators B 5:139-144.
Mastrototaro et al., 2003. Reproducibility of the continuous glucose monitoring system matches previous reports and the intended use of the product. Diabetes Care 26:256; author reply p. 257.

(56) References Cited

OTHER PUBLICATIONS

Mastrototaro, J. J. 2000. The MiniMed continuous glucose monitoring system. Diabetes Technology & Therapeutics 2(Suppl 1):S13-8.

Matsumoto et al., 1998. A micro-planar amperometeric glucose sensor unsusceptible to interference species. Sensors and Actuators B 49:68-72.

Matsumoto et al., 2001. A long-term lifetime amperometric glucose sensor with a perfluorocarbon polymer coating. Biosensors & Bioelectronics 16:271-276.

Matthews et al., 1988. An amperometric needle-type glucose sensor testing in rats and man. Diabetic Medicine 5:248-252.

McCartney et al., 2001. Near-infrared fluorescence lifetime assay for serum glucose based on allophycocyanin-labeled concanavalin A. Analytical Biochemistry 292:216-221.

McGrath et al., 1995. The use of differential measurements with a glucose biosensor for interference compensation during glucose determinations by flow injection analysis. Biosensors & Bioelectronics 10:937-943.

McKean, et al., Jul. 7, 1988. A Telemetry Instrumentation System for Chronically Implanted Glucose and Oxygen Sensors. Transactions on Biomedical Engineering 35:526-532.

Memoli et al., 2002. A comparison between different immobilised glucoseoxidse-based electrodes. J Pharm Biomed Anal 29:1045-1052.

Meyerhoff et al., 1992. On line continuous monitoring of subcutaneous tissue glucose in men by combining portable glucosensor with microdialysis. Diabetologia 35:1087-1092.

Miller et al., 1989. Generation of IL1-like activity in response to biomedical polymer implants: a comparison of in vitro and in vivo models. J Biomedical Materials Research 23:1007-1026.

Miller et al., 1989. In vitro stimulation of fibroblast activity by factors generated from human monocytes activated by biomedical polymers. J Biomedical Materials Research 23:911-930.

Miller, A. 1988. Human monocyte-macrophage activation and interleukin 1 generation by biomedical polymers. J Biomedical Materials Research 23:713-731.

Minale et al., Sep. 1988. Clinical Experience with Expanded Plytetrafluoroethylene Gore-Tex® Surgical Membrane for Pericardial Closure: A Study of 110 Cases. J Cardiac Surgery 3(3): 193-201.

Moatti-Sirat et al., 1992. Evaluating in vitro and in vivo the interference of ascorbate and acetaminophen on glucose detection by a needle-type glucose sensor. Biosensors & Bioelectronics 7:345-352.

Moatti-Sirat et al., 1992. Towards continuous glucose monitoring: in vivo evaluation of a miniaturized glucose sensor implanted for several days in rat subcutaneous tissue. Diabetologia 35:224-230.

Moatti-Sirat et al., Jun. 1994. Reduction of acetaminophen interference in glucose sensors by a composite Nafion membrane: demonstration in rats and man. Diabetologia 37(6):610-616.

Morff et al., 1990. Microfabrication of reproducible, economical, electroenzymatic glucose sensors. Annual International Conference of the IEEE Engineering in Medicine and Biology Society 12(2):0483-0484.

Mosbach et al., 1975. Determination of heat changes in the proximity of immobilized enzymes with an enzyme termistor and its use for the assay of metabolites. Biochim. Biophys. Acta.(Enzymology) 403:256-265.

Motonaka et al., 1993. Determination of cholesterol and cholesterol ester with novel enzyme microsensors. Analytical Chemistry 65:3258-3261.

Moussy et al., 2000. Biomaterials community examines biosensor biocompatibility, Diabetes Technology & Therapeutics 2:473-477.

Mowery et al., 2000. Preparation and characterization of hydrophobic polymeric films that are thromboresistant via nitric oxide release. Biomaterials 21:9-21.

Murphy, et al., 1992. Polymer membranes in clinical sensor applications. II. The design and fabrication of permselective hydrogels for electrochemical devices. Biomaterials 13(14):979-990.

Muslu. 1991. Trickling filter performance. Applied Biochemistry and Biotechnology 37:211-224.

Myler et al., 2002. Ultra-thin-polysiloxane-film-composite membranes for the optimisation of amperometric oxidase enzyme electrodes. Biosensors & Bioelectronics 17:35-43.

Nakayama et al., 1992. Surface fixation of hydrogels: heparin and glucose oxidase hydrogelated surfaces. ASAIO Journal 38:M421-M424.

Nam et al., 2000. A novel fabrication method of macroporous biodegradable polymer scaffolds using gas foaming salt as a porogen additive. J Biomedical Materials Research 53:1-7.

Ohara et al., 1994. "Wired" enzyme electrodes for amperometric determination of glucose or lactate in the presence of interfering substances. Analytical Chemistry 66:2451-2457.

Ohara, et al., Dec. 1993. Glucose electrodes based on cross-linked bis(2,2'-bipyridine)chloroosmium(+-2+) complexed poly(I-vinylimidazole) films. Analytical Chemistry 65:3512-3517.

Okuda et al., 1971. Mutarotase effect on micro determinations of D-glucose and its anomers with (3-D-glucose oxidase. Analytical Biochemistry 43:312-315.

Palmisano et al., 2000. Simultaneous monitoring of glucose and lactate by an interference and crosstalk free dual electrode amperometric biosensor based on electropolymerized thin films. Biosensors & Bioelectronics 15:531-539.

Panetti 2002. Differential effects of sphingosine 1-phosphate and lysophosphatidic acid on endothelial cells. Biochimica et Biophysica Acta 1582:190-196.

Patel et al., 2003. Amperometric glucose sensors based on ferrocene containing polymeric electron transfer systems—a preliminary report. Biosensors & Bioelectronics 18:1073-1076.

Pegoraro et al., 1995. Gas transport properties of siloxane polyurethanes. Journal of Applied Polymer Science 57:421-429.

Pfeiffer et al., 1992. On line continuous monitoring of subcutaneous tissue glucose is feasible by combining portable glucosensor with microdialysis. Horm. Metab. Res. 25:121-124.

Pfeiffer, E.F. 1990. The glucose sensor: the missing link in diabetes therapy. Horm Metab Res Suppl. 24:154-164.

Phillips and Smith. 1988. Biomedical Applications of Polyurethanes: Implications of Failure Mechanisms. J. Biomaterial Appleiations 3:202-227.

Pichert et al., 2000. Issues for the coming age of continuous glucose monitoring. Diabetes Educator 26(6):969-980.

Pickup et al. 1987-88. Implantable glucose sensors: choosing the appropriate sensing strategy. Biosensors 3:335-346 (1987-88).

Pickup et al., 1989. In vivo molecular sensing in diabetes mellitus: an implantable glucose sensor with direct electron transfer. Diabetologia 32:213-217.

Pickup et al., 1989. Potentially-implantable, amperometric glucose sensors with mediated electron transfer: improving the operating stability. Biosensors 4:109-119.

Pineda et al., 1996. Bone regeneration with resorbable polymeric membranes. III. Effect of poly(L-lactide) membrane pore size on the bone healing process in large defects. J. Biomedical Materials Research 31:385-394.

Pinner et al., Oct. 24, 1959. Cross-linking of cellulose acetate by ionizing radiation. Nature 184:1303-1304.

Pishko et al., 1991. Amperometric glucose microelectrodes prepared through immobilization of glucose oxidase in redox hydrogels. Analytical Chemistry 63:2268-2272.

Pitzer et al., 2001. Detection of hypoglycemia with the GlucoWatch biographer. Diabetes Care 24(5):881-885.

Poitout et al., 1991. In Vitro and In Vivo Evaluation in Dogs of a Miniaturized Glucose Sensor. ASAIO Transactions 37:M298-M300.

Poitout et al., 1993. A glucose monitoring system for on line estimation in man of blood glucose concentration using a miniaturized glucose sensor implanted in the subcutaneous tissue and a wearable control unit. Diabetologia 36:658-663.

Poitout et al., 1994. Development of a glucose sensor for glucose monitoring in man: the disposable implant concept. Clinical Materials 15:241-246.

(56) References Cited

OTHER PUBLICATIONS

Postlethwaite et al., 1996. Interdigitated array electrode as an alternative to the rotated ring-disk electrode for determination of the reaction products of dioxygen reduction. Analytical Chemistry 68:2951-2958.
Prabhu et al., 1981. Electrochemical studies of hydrogen peroxide at a platinum disc electrode. Electrochimica Acta 26(6):725-729.
Preclude® Pericardial Membrane Brochure, Nov. 2001, W.L. Gore & Associates, Inc., Flagstaff, AZ 86004.
Quinn et al., 1995. Kinetics of glucose delivery to subcutaneous tissue in rats measured with 0.3-mm amperometric microsensors. The American Physiological Society E155-E161.
Quinn et al., 1997. Biocompatible, glucose-permeable hydrogel for in situ coating of implantable biosensors. Biomaterials 18:1665-1670.
Rabah et al., 1991. Electrochemical wear of graphite anodes during electrolysis of brine. Carbon 29(2):165-171.
Ratner, B.D. 2002. Reducing capsular thickness and enhancing angiogenesis around implant drug release systems. J Controlled Release 78:211-218.
Reach et al., 1986. A Method for Evaluating in vivo the Functional Characteristics of Glucose Sensors. Biosensors 2:211-220.
Reach et al., 1992. Can continuous glucose monitoring be used for the treatment of diabetes? Analytical Chemistry 64(5):381-386.
Reach, Gerard. 2000-2001. Letters to the Editor Re: Diabetes Technology & Therapeutics 2:49-56 (2000); Diabetes Technology & Therapeutics 3(1): 129-130 (2001).
Rebrin et al., 1989. Automated feedback control of subcutaneous glucose concentration in diabetic dogs. Diabetologia 32:573-576.
Rebrin et al., 1992. Subcutaneous glucose monitoring by means of electrochemical sensors: fiction or reality? J. Biomed. Eng. 14:33-40.
Revuelta et al., Mar. 1985. Expanded Polytetrafluoroethylene Surgical Membrane for Pericardial Closure. J Thorac Cardiovascular Surgery 89(3):451-455.
Rhodes et al., 1994. Prediction of pocket-portable and implantable glucose enzyme electrode performance from combined species permeability and digital simulation analysis. Analytical Chemistry 66(9):1520-1529.
Rivers et al., 2001. Central venous oxygen saturation monitoring in the critically ill patient. Current Opinion in Critical Care 7:204-211.
Sakakida et al., 1992. Development of Ferrocene-Mediated Needle-Type Glucose Sensor as a Measure of True Subcutaneous Tissue Glucose Concentrations. Artificial Organs Today 2(2):145-158.
Sakakida et al., 1993. Ferrocene-Mediated Needle Type Glucose Sensor Covered with Newly Designed Biocompatible Membrane. Sensors and Actuators B 13-14:319-322.
Sansen et al., 1985. Glucose sensor with telemetry system. In Ko, W. H. (Ed.). Implantable Sensors for Closed Loop Prosthetic Systems. Chap. 12, pp. 167-175, Mount Kisco, NY: Futura Publishing Co.
Sansen et al., 1990. A smart sensor for the voltammetric measurement of oxygen or glucose concentrations. Sensors and Actuators B 1:298-302.
Schmidt et al., 1993. Glucose concentration in subcutaneous extracellular space. Diabetes Care 16(5):695-700.
Schmidtke et al., Jan. 1998, Measurement and modeling of the transient difference between blood and subcutaneous glucose concentrations in the rat after injection of insulin, Proc Natl Acad Sci USA 95:294-299.
Schoemaker et al., 2003. The SCGM1 system: Subcutaneous continuous glucose monitoring based on microdialysis technique. Diabetes Technology & Therapeutics 5(4):599-608.
Schoonen et al., 1990. Development of a potentially wearable glucose sensor for patients with diabetes mellitus: design and in-vitro evaluation. Biosensors & Bioelectronics 5:37-46.
Schuler et al., 1999. Modified gas-permeable silicone rubber membranes for covalent immobilisation of enzymes and their use in biosensor development. Analyst 124:1181-1184.
Selam, J. L. 1997. Management of diabetes with glucose sensors and implantable insulin pumps. From the dream of the 60s to the realities of the 90s. ASAIO Journal 43:137-142.
Service et al., 1970. Mean amplitude of glycemic excursions, a measure of diabetic instability. Diabetes 19:644-655.
Service, R. F. 2002. Can sensors make a home in the body? Science 297:962-3.
Sharkawy et al., 1996. Engineering the tissue which encapsulates subcutaneous implants. I. Diffusion properties. J Biomedical Materials Research 37:401-412.
Shaw et al., 1991. In vitro testing of a simply constructed, highly stable glucose sensor suitable or implantation in diabetic patients. Biosensors & Bioelectronics 6:401-406.
Shichiri et al., 1982. Wearable artificial endocrine pancreas with needle-type glucose sensor. Lancet 2:1129-1131.
Shichiri et al., 1983. Glycaemic Control in Pancreatectomized Dogs with a Wearable Artificial Endocrine Pancreas. Diabetologia 24:179-184.
Shichiri et al., 1985. Needle-type Glucose Sensor for Wearable Artificial Endocrine Pancreas, in Implantable Sensors for Closed-Loop Prosthetic Systems, Ed. Ko, Future Publishing Co., Mt. Kisko, NY, pp. 197-210.
Shichiri et al., 1986. Telemetry Glucose Monitoring Device with Needle-Type Glucose Sensor: A Useful Tool for Blood Glucose Monitoring in Diabetic Individuals. Diabetes Care 9(3):298-301.
Shichiri et al., 1989. Membrane Design for Extending the Long-Life of an Implantable Glucose Sensor. Diab. Nutr. Metab. 2:309-313.
Shults et al., 1994. A telemetry-instrumentation system for monitoring multiple subcutaneously implanted glucose sensors. IEEE Transactions on Biomedical Engineering 41(10):937-942.
Sieminski et al., 2000. Biomaterial-microvasculature interactions. Biomaterials 21:2233-2241.
Skyler, J. S. 2000. The economic burden of diabetes and the benefits of improved glycemic control: The potential role of a continuous glucose monitoring system. Diabetes Technology & Therapeutics 2(Suppl 1):S7-S12.
Sokol et al., 1980. Immobilized-enzyme rate-determination method for glucose analysis. Clinical Chemistry 26(1):89-92.
Sriyudthsak et al., 1996. Enzyme-epoxy membrane based glucose analyzing system and medical applications. Biosensors & Bioelectronics 11:735-742.
Steil et al., 2003. Determination of plasma glucose during rapid glucose excursions with a subcutaneous glucose sensor. Diabetes Technology & Therapeutics 5(1):27-31.
Stern et al., 1957. Electrochemical polarization: 1. Atheoretical analysis of the shape of polarization curves. Journal of the Electrochemical Society 104(1):56-63.
Sternberg et al., 1988. Covalent enzyme coupling on cellulose acetate membranes for glucose sensor development. Analytical Chemistry 69:2781-2786.
Sternberg et al., 1988. Study and Development of Multilayer Needle-type Enzyme-based Glucose Microsensors. Biosensors 4:27-40.
Stokes. 1988, Polyether Polyurethanes: Biostable or Not? J. Biomaterial Applications 3:228-259.
Sumino T. et al., 1998. Preliminary study of continuous glucose monitoring with a microdialysis technique. Proceedings of the IEEE 20(4): 1775-1778.
Takegami et al., 1992. Pervaporation of ethanol water mixtures using novel hydrophobic membranes containing polydimethylsiloxane. Journal of Membrane Science 75:93-105.
Tanenberg et al., 2000. Continuous glucose monitoring system: A new approach to the diagnosis of diabetic gastroparesis. Diabetes Technology & Therapeutics 2(Suppl 1):S73-S80.
Tang et al., 1993. Fibrin(ogen) mediates acute inflammatory responses to biomaterials. J Exp Med 178:2147-2156.
Tang et al., 1995. Inflammatory responses to biomaterials. American J Clinical Pathology 103:466-471.
Tang et al., 1996. Molecular determinants of acute inflammatory responses to biomaterials. J Clinial Investigation97:1329-1334.
Tang et al., 1998. Mast cells mediate acute inflammatory responses to implanted biomaterials. Proc Natl Acad Sci USA 95:8841-8846.

(56) References Cited

OTHER PUBLICATIONS

Tatsuma et al., 1991. Oxidase-peroxidase bilayer-modified electrodes as sensors for lactate, pyruvate, cholesterol and uric acid. Analytica Chimica Acta 242:85-89.
Thome et al., 1995. Can the decrease in subcutaneous glucose concentration precede the decrease in blood glucose level? Proposition for a push-pull kinetics hypothesis. Horm. Metab. Res. 27:53 (Abstract).
Thome-Duret et al., 1996. Modification of the sensitivity of glucose sensor implanted into subcutaneous tissue. Diabetes Metabolism 22:174-178.
Thome-Duret et al., 1996. Use of a subcutaneous glucose sensor to detect decreases in glucose concentration prior to observation in blood. Analytical Chemistry 68:3822-3826.
Thome-Duret et al., 1998. Continuous glucose monitoring in the free-moving rat. Metabolism 47:799-803.
Thompson et al., 1986. In Vivo Probes: Problems and Perspectives. Department of Chemistry, University of Toronto, Canada, pp. 255-261.
Tibell et al., 2001. Survival of macroencapsulated allogeneic parathyroid tissue one year after transplantation in nonimmunosuppressed humans. Cell Transplant 10:591-9.
Tierney et al., 2000. Effect of acetaminophen on the accuracy of glucose measurements obtained with the GlucoWatch biographer. Diabetes Technology & Therapeutics 2:199-207.
Tierney et al., 2000. The GlucoWatch® biographer: A frequent, automatic and noninvasive glucose monitor. Ann. Med. 32:632-641.
Trecroci, D. 2002. A Glimpse into the Future-Continuous Monitoring of Glucose with a Microfiber. Diabetes Interview Jul. 2002, pp. 42-43.
Tse and Gough. 1987. Time-Dependent Inactivation of Immobilized Glucose Oxidase and Catalase. Biotechnol. Bioeng. 29:705-713.
Turner and Pickup, 1985. Diabetes mellitus: biosensors for research and management. Biosensors 1:85-115.
Turner et al., 1984. Carbon Monoxide: Acceptor Oxidoreductase from Pseudomonas Thermocarboxydovorans Strain C2 and its use in a Carbon Monoxide Sensor. Analytica Chimica Acta 163: 161-174.
Turner, A.P.F. 1988. Amperometric biosensor based on mediator-modified electrodes. Methods in Enzymology 137:90-103.
Updike et al., 1967, The enzyme electrode. Nature 214:986-988.
Updike et al., 1982. Implanting the glucose enzyme electrode: Problems, progress, and alternative solutions. Diabetes Care 5(3):207-212.
Updike et al., 1988. Laboratory Evaluation of New Reusable Blood Glucose Sensor. Diabetes Care 11:801-807.
Updike et al., 1994. E nzymatic glucose sensor: Improved long-term performance in vitro and in vivo. ASAIO Journal 40(2):157-163.
Updike et al., 1997. Principles of long-term fully implanted sensors with emphasis on radiotelemetric monitoring of blood glucose form inside a subcutaneous foreign body capsule (FBC). In Fraser, ed., Biosensors in the Body. New York. John Wiley & Sons, Chapter 4, pp. 117-137.
Updike et al., 2000. A subcutaneous glucose sensor with improved longevity, dynamic range, and stability of calibration. Diabetes Care 23(2):208-214.
Vadgama, P. Nov. 1981. Enzyme electrodes as practical biosensors. Journal of Medical Engineering & Technology 5(6):293-298.
Vadgama. 1988. Diffusion limited enzyme electrodes. NATO ASI Series: Series C, Math and Phys. Sci. 226:359-377.
Velho et al., 1989. In vitro and in vivo stability of electrode potentials in needle-type glucose sensors. Influence of needle material. Diabetes 38:164-171.
Velho et al., 1989. Strategies for calibrating a subcutaneous glucose sensor. Biomed Biochim Acta 48(11-12): 957-964.
von Woedtke et al., 1989. In situ calibration of implanted electrochemical glucose sensors. Biomed Biochim. Acta 48(11-12):943-952.
Wade Jr., L.G. Organic Chemistry, Chapter 17, Reactions of Aromatic Compounds pp. 762-763, 1987.

Wagner et al., 1998. Continuous amperometric monitoring of glucose in a brittle diabetic chimpanzee with a miniature subcutaneous electrode. Proc. Natl. Acad. Sci. A 95:6379-6382.
Wang et al., 1994. Highly Selective Membrane-Free, Mediator-Free Glucose Biosensor, Analytical Chemistry 66:3600-3603.
Wang et al., 1997. Improved ruggedness for membrane-based amperometric sensors using a pulsed amperometric method. Analytical Chemistry 69:4482-4489.
Ward et al., 2000. Rise in background current overtime in a subcutaneous glucose sensor in the rabbit: Relevance to calibration and accuracy. Biosensors & Bioelectronics 15:53-61.
Ward et al., 2000. Understanding Spontaneous Output Fluctuations of an Amperometric Glucose Sensor: Effect of Inhalation Anesthesia and e of a Nonenzyme Containing Electrode. ASAIO Journal 46:540-546.
Ward et al., 2002. A new amperometric glucose microsensor: In vitro and short-term in vivo evaluaton. Biosensors & Bioelectronics 17:181-189.
Wientjes, K. J. C. 2000. Development of a glucose sensor for diabetic patients (Ph.D. Thesis).
Wilkins et al., 1988. The coated wire electrode glucose sensor. Horm Metab Res Suppl. 20:50-55.
Wilkins et al., 1995. Glucose monitoring: state of the art and future possibilities. Med Eng Phys 18:273-288.
Wilkins et al., 1995, Integrated implantable device for long-term glucose monitoring. Biosensors & Bioelectronics 10:485-494.
Wilson et al., 1992. Progress toward the development of an implantable sensor for glucose. Clinical Chemistry 38(9):1613-1617.
Wilson et al., 2000, Enzyme-based biosensors for in vivo measurements. Chem. Rev, 100:2693 2704.
Wood, W. et al., Mar. 1990, Hermetic Sealing with Epoxy. Mechanical Engineering (3 pages).
Woodward. 1982. How Fibroblasts and Giant Cells Encapsulate Implants: Considerations in Design of Glucose Sensor. Diabetes Care 5:278-281.
Wright et al., 1999. Bioelectrochemical dehalogenations via direct electrochemistry of poly(ethylene oxide)-modified myoglobin. Electrochemistry Communications 1: 603-611.
Wu et al., 1999. In situ electrochemical oxygen generation with an immunoisolation device. Annals of the New York Academy of Sciences, pp. 105-125.
Yang et al., 1996. A glucose biosensor based on an oxygen electrode: In-vitro performances in a model buffer solution and in blood plasma. Biomedical Instrumentation & Technology 30:55-61.
Yang et al., 1998. Development of needle-type glucose sensor with high selectivity. Sensors and Actuators B 46:249-256.
Ye et al., 1993. High Current Density 'Wired' Quinoprotein Glucose Dehydrogenase Electrode. Analytical Chemistry 65:238-241.
Zamzow et al., 1990. Development and evaluation of a wearable blood glucose monitor. ASAIO Transactions 36(3):M588-M591.
Zhang et al., 1993. Electrochemical oxidation of H202 on Pt and Pt + Ir electrodes in physiological buffer and its applicablilty to H202-based biosensors. J. Electroanalytical Chemistry 345:253-271.
Zhang et al., 1993. In vitro and in vivo evaluation of oxygen effects on a glucose oxidase based implantable glucose sensor. Analytica Chimica Acta 281:513-520.
Zhang et al., 1994. Elimination of the acetaminophen interference in an implantable glucose sensor. Analytical Chemistry 66(7):1183-1188.
Zhu et al., 1994. Fabrication and characterization of glucose sensors based on a microarray H202 electrode. Biosensors & Bioelectronics 9: 295-300.
EP App. No. 02747094.7, filed Jul. 26, 2002: Office Action dated Nov. 19, 2004.
JP App. No. 2003-516584, filed Jul. 26, 2002 [Appeal No. 084163]: Appeal Decision dated Sep. 1, 2009.
PCT/US2002/023902, filed Jul. 26, 2002: International Preliminary Examination Report.
PCT/US2002/023902, filed Jul. 26, 2002: International Search Report.
U.S. Appl. No. 08/811,473: Office Action dated Dec. 7, 1998.
U.S. Appl. No. 09/447,227: Office Action dated Apr. 4, 2006.

(56) References Cited

OTHER PUBLICATIONS

U.S. Appl. No. 09/447,227: Office Action dated Aug. 1, 2006.
U.S. Appl. No. 09/447,227: Office Action dated Aug. 15, 2001.
U.S. Appl. No. 09/447,227: Office Action dated Dec. 11, 2008.
U.S. Appl. No. 09/447,227: Office Action dated Jan. 16, 2003.
U.S. Appl. No. 09/447,227: Office Action dated Jan. 17, 2002.
U.S. Appl. No. 09/447,227: Office Action dated Jan. 23, 2008.
U.S. Appl. No. 09/447,227: Office Action dated Jul. 15, 2002.
U.S. Appl. No. 09/447,227: Office Action dated Jul. 17, 2007.
U.S. Appl. No. 09/447,227: Office Action dated Jul. 9, 2003.
U.S. Appl. No. 09/447,227: Office Action dated Jun. 12, 2008.
U.S. Appl. No. 09/447,227: Office Action dated Mar. 9, 2007.
U.S. Appl. No. 09/447,227: Office Action dated May 26, 2009.
U.S. Appl. No. 09/447,227: Office Action dated Nov. 28, 2003.
U.S. Appl. No. 09/447,227: Office Action dated Sep. 22, 2005.
U.S. Appl. No. 09/489,588: Office Action dated Aug. 14, 2001.
U.S. Appl. No. 09/489,588: Office Action dated Feb. 27, 2002.
U.S. Appl. No. 09/489,588: Office Action dated Jun. 12, 2003.
U.S. Appl. No. 09/916,386: Office Action dated Apr. 9, 2003.
U.S. Appl. No. 09/916,858: Office Action dated Mar. 22, 2004.
U.S. Appl. No. 09/916,858: Office Action dated Sep. 21, 2004.
U.S. Appl. No. 10/646,333: Office Action dated Feb. 24, 2006.
U.S. Appl. No. 10/646,333: Office Action dated Jun. 6, 2005.
U.S. Appl. No. 10/646,333: Office Action dated Sep. 22, 2004.
U.S. Appl. No. 10/647,065: Office Action dated Oct. 16, 2006.
U.S. Appl. No. 10/657,843: Office Action dated Sep. 21, 2004.
U.S. Appl. No. 10/838,909: Office Action mailed Jun. 5, 2008.
U.S. Appl. No. 10/838,909: Office Action mailed Mar. 16, 2009.
U.S. Appl. No. 10/838,912: Office Action dated Jul. 16, 2008.
U.S. Appl. No. 10/838,912: Office Action dated Mar. 24, 2008.
U.S. Appl. No. 10/838,912: Office Action dated Sep. 21, 2007.
U.S. Appl. No. 10/846,150: Office Action dated Dec. 9, 2008.
U.S. Appl. No. 10/846,150: Office Action dated Jun. 5, 2008.
U.S. Appl. No. 10/846,150: Office Action dated Jun. 9, 2009.
U.S. Appl. No. 11/039,269: Office Action dated Aug. 14, 2006.
U.S. Appl. No. 11/039,269: Office Action dated Feb. 24, 2006.
U.S. Appl. No. 11/039,269: Office Action dated May 4, 2005.
U.S. Appl. No. 11/039,269: Office Action dated Nov. 2, 2005.
U.S. Appl. No. 11/055,779: Office Action dated May 23, 2007.
U.S. Appl. No. 11/055,779: Office Action dated Oct. 24, 2007.
U.S. Appl. No. 11/439,630: Office Action dated Feb. 23, 2009.
U.S. Appl. No. 11/439,630: Office Action dated Sep. 18, 2008.
U.S. Appl. No. 11/503,367: Office Action dated Dec. 1 2008.
U.S. Appl. No. 12/037,812: Office Action dated Apr. 1.
U.S. Appl. No. 12/037,812: Office Action dated Jul. 24, 2009.
U.S. Appl. No. 12/037,812: Office Action dated Sep. 29, 2008.
U.S. Appl. No. 12/037,830: Office Action dated Feb. 26, 2009.
U.S. Appl. No. 12/037,830: Office Action dated Sep. 29, 2008.
U.S. Reexamination Control No. 90/011067: Electronic File History through Jan. 3, 2010, including Office Action dated Oct. 29, 2010 and Applicant Response filed Dec. 29, 2010.
U.S. Reexamination Control No. 90/011080: Electronic File History through Jan. 3, 2010, including Office Action dated Oct. 29, 2010 and Applicant Response filed Dec. 29, 2010.
Alberts et al., 1994. Molecular Biology of the Cell, $3^{rd}$ Ed., p. G-19.
Dobson et al., Apr. 1990. 1-Butyrul-glycerol: A novel angioge3nesis factor secreted by differentiating adipocytes. Cell 61(2):223-230.
English et al., Feb. 2001. Platelet-released phospholipids link haemostasis and angiogenesis. Cardiovascular Research 49:588-599.
Halvorsen et al., Dec. 1993 Vasodilation of rat retinal microvessels induced by monobutyrin. J. Clinical Investigation 92(6):2872-2876.
Kidd et al., Nov. 2001: Angiogenesis and neovascular associated with extracellular matrix-modified porous implants. J. Biomedical Materials Research 59(2):366-377.
Kugler et al., Aug. 1990. A new steroid-eluting epicardial lead: Experience with atrial and ventricular implantation in the immature swine. PACE 13:976-981.
Mathivanar et al., Dec. 1990. In vivo elution rate of drug eluting ceramic leads with a reduced dose of dexamethasone sodium phosphate. PACE 13(II):1883-1886.
Mond et al., Jan. 1992. The electrode-tissue interface: the revolutionary role of steroid elution. PACE 15:95-107.
Radovsky et al., Jan. 1989. Effects of dexamethasone elution on tissue reaction around stimulating electrodes of endocardial pacing leads in dogs. Am. Heart J. 117:1288-1297.
Ward et al., 1999. Assessment of chronically implanted subcutaneous glucose sensors in dogs: the effect of surrounding fluid masses. ASAIO Journal 45:555-561.

MEMBRANE FOR USE WITH IMPLANTABLE DEVICES

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 12/633,578 filed Dec. 8, 2009, which is a continuation of U.S. application Ser. No. 10/768,889 filed Jan. 29, 2004, now U.S. Pat. No. 7,632,228, which is a continuation of U.S. application Ser. No. 09/916,386, filed Jul. 27, 2001, now U.S. Pat. No. 6,702,857. Each of the aforementioned applications is incorporated by reference herein in its entirety, and each is hereby expressly made a part of this specification.

FIELD OF THE INVENTION

The present invention relates generally to biointerface membranes that may be utilized with implantable devices such as devices for the detection of analyte concentrations in a biological sample, cell transplantation devices, drug delivery devices and electrical signal delivering or measuring devices. The present invention further relates to methods for determining analyte levels using implantable devices including these membranes. More particularly, the invention relates to novel biointerface membranes, to sensors and implantable devices including these membranes, and to methods for monitoring glucose levels in a biological fluid sample using an implantable analyte detection device.

BACKGROUND OF THE INVENTION

One of the most heavily investigated analyte sensing devices is an implantable glucose sensor for detecting glucose levels in patients with diabetes. Despite the increasing number of individuals diagnosed with diabetes and recent advances in the field of implantable glucose monitoring devices, currently used devices are unable to provide data safely and reliably for long periods of time (e.g., months or years) [See, e.g., Moatti-Sirat et al., Diabetologia 35:224-30 (1992)]. There are two commonly used types of implantable glucose sensing devices. These types are those which are implanted intravascularly and those implanted in tissue.

With reference to devices that may be implanted in tissue, a disadvantage of these devices has been that they tend to lose their function after the first few days to weeks following implantation. At least one reason for this loss of function has been attributed to the fact that there is no direct contact with circulating blood to deliver sample to the tip of the probe of the implanted device. Because of these limitations, it has previously been difficult to obtain continuous and accurate glucose levels. However, this information is often extremely important to diabetic patients in ascertaining whether immediate corrective action is needed in order to adequately manage their disease.

Some medical devices, including implanted analyte sensors, drug delivery devices and cell transplantation devices require transport of solutes across the device-tissue interface for proper function. These devices generally include a membrane, herein referred to as a cell-impermeable membrane that encases the device or a portion of the device to prevent access by host inflammatory or immune cells to sensitive regions of the device.

A disadvantage of cell-impermeable membranes is that they often stimulate a local inflammatory response, called the foreign body response (FBR) that has long been recognized as limiting the function of implanted devices that require solute transport. Previous efforts to overcome this problem have been aimed at increasing local vascularization at the device-tissue interface with limited success.

The FBR has been well described in the literature and is composed of three main layers, as illustrated in FIG. 1. The innermost FBR layer 40, adjacent to the device, is composed generally of macrophages and foreign body giant cells 41 (herein referred to as the barrier cell layer). These cells form a monolayer 40 of closely opposed cells over the entire surface 48a of a smooth or microporous (<1.0 .mu.m) membrane 48. The intermediate FBR layer 42 (herein referred to as the fibrous zone), lying distal to the first layer with respect to the device, is a wide zone (30-100 microns) composed primarily of fibroblasts 43 and fibrous matrix 44. The outermost FBR layer 46 is loose connective granular tissue containing new blood vessels 45 (herein referred to as the vascular zone 46). A consistent feature of the innermost layers 40 and 42 is that they are devoid of blood vessels. This has led to widely supported speculation that poor transport of molecules across the device-tissue interface 47 is due to a lack of vascularization near interface 47 (Scharp et al., World J. Surg. 8:221-229 (1984), Colton and Avgoustiniatos J. Biomech. Eng. 113:152-170 (1991)).

Patents by Brauker et al. (U.S. Pat. No. 5,741,330), and Butler et al. (U.S. Pat. No. 5,913,998), describe inventions aimed at increasing the number of blood vessels adjacent to the implant membrane (Brauker et al.), and growing within (Butler et al.) the implant membrane at the device-tissue interface. The patent of Shults et al. (U.S. Pat. No. 6,001,067) describes membranes that induce angiogenesis at the device-tissue interface of implanted glucose sensors. FIG. 2 illustrates a situation in which some blood vessels 45 are brought close to an implant membrane 48, but the primary layer 40 of cells adherent to the cell-impermeable membrane blocks glucose. This phenomenon is described in further detail below.

In the examples of Brauker et al. (supra), and Shults et al., bilayer membranes are described that have cell impermeable layers that are porous and adhesive to cells. Cells are able to enter into the interstices of these membranes, and form monolayers on the innermost layer, which is aimed at preventing cell access to the interior of the implanted device (cell impenetrable layers). Because the cell impenetrable layers are porous, cells are able to reach pseudopodia into the interstices of the membrane to adhere to and flatten on the membrane, as shown in FIGS. 1 and 2, thereby blocking transport of molecules across the membrane-tissue interface. The known art purports to increase the local vascularization in order to increase solute availability. However, the present studies show that once the monolayer of cells (barrier cell layer) is established adjacent to the membrane, increasing angiogenesis is not sufficient to increase transport of molecules such as glucose and oxygen across the device-tissue interface.

One mechanism of inhibition of transport of solutes across the device-tissue interface that has not been previously discussed in the literature is the formation of a uniform barrier to analyte transport by cells that form the innermost layer of the foreign body capsule. This layer of cells forms a monolayer with closely opposed cells having tight cell-to-cell junctions. When this barrier cell layer forms, it is not substantially overcome by increased local vascularization. Regardless of the level of local vascularization, the barrier cell layer prevents the passage of molecules that cannot diffuse through the layer. Again, this is illustrated in FIG. 2 where blood vessels 45 lie adjacent to the membrane but glucose transport is significantly reduced due to the impermeable nature of the barrier cell layer 40. For example, both glucose and its phosphorylated form do not readily transit the cell membrane and consequently little glucose reaches the implant membrane through the barrier layer cells.

It has been confirmed by the present inventors through histological examination of explanted sensors that the most likely mechanism for inhibition of molecular transport across the device-tissue interface is the barrier cell layer adjacent to the membrane. There is a strong correlation between desired device function and the lack of formation of a barrier cell layer at the device-tissue interface. In the present studies, devices that were observed histologically to have substantial barrier cell layers were functional only 41% of the time after 12 weeks in vivo. In contrast, devices that did not have significant barrier cell layers were functional 86% of the time after 12 weeks in vivo.

Consequently, there is a need for a membrane that interferes with the formation of a barrier layer and protects the sensitive regions of the device from host inflammatory response.

SUMMARY OF THE INVENTION

The biointerface membranes of the present invention interfere with the formation of a monolayer of cells adjacent to the membrane, henceforth referred to herein as a barrier cell layer, which interferes with the transport of oxygen and glucose across a device-tissue interface.

It is to be understood that various biointerface membrane architectures (e.g., variations of those described below) are contemplated by the present invention and are within the scope thereof.

In one aspect of the present invention, a biointerface membrane for use with an implantable device is provided including; a first domain distal to the implantable device wherein the first domain supports tissue ingrowth and interferes with barrier-cell layer formation and a second domain proximal to the implantable device wherein the second domain is resistant to cellular attachment and is impermeable to cells and cell processes.

In another aspect of the present invention, a biointerface membrane is provided including the properties of: promoting tissue ingrowth into; interfering with barrier cell formation on or within; resisting barrier-cell attachment to; and blocking cell penetration into the membrane.

In yet another aspect, a sensor head for use in an implantable device is provided which includes a biointerface membrane of the present invention.

In other aspects, a sensor for use in an implantable device that measures the concentration of an analyte in a biological fluid is provided including the biointerface membrane of the present invention.

In still another aspect of the present invention, a device for measuring an analyte in a biological fluid is provided, the device including the biointerface membrane of the present invention, a housing which includes electronic circuitry, and at least one sensor as provided above operably connected to the electronic circuitry of the housing.

The present invention further provides a method of monitoring analyte levels including the steps of: providing a host, and an implantable device as provided above; and implanting the device in the host. In one embodiment, the device is implanted subcutaneously.

Further provided by the present invention is a method of measuring analyte in a biological fluid including the steps of: providing i) a host, and ii) a implantable device as provided above capable of accurate continuous analyte sensing; and implanting the device in the host. In one embodiment of the method, the device is implanted subcutaneously.

In still another aspect of the present invention, an implantable drug delivery device is provided including a biointerface membrane as provided above. Preferably the implantable drug delivery device is a pump, a microcapsule or a macrocapsule.

The present invention further provides a device for implantation of cells which includes a biointerface membrane as provided above.

Also encompassed by the present invention is an electrical pulse delivering or measuring device, including a biointerface membrane according to that provided above.

The biointerface membranes, devices including these membranes and methods of use of these membranes provided by the invention allow for long term protection of implanted cells or drugs, as well as continuous information regarding, for example, glucose levels of a host over extended periods of time. Because of these abilities, the biointerface membranes of the present invention can be extremely important in the management of transplant patients, diabetic patients and patients requiring frequent drug treatment.

DEFINITIONS

In order to facilitate an understanding of the present invention, a number of terms are defined below.

The terms "biointerface membrane," and the like refer to a permeable membrane that functions as a device-tissue interface comprised of two or more domains. Preferably, the biointerface membrane is composed of two domains. The first domain supports tissue ingrowth, interferes with barrier cell layer formation and includes an open cell configuration having cavities and a solid portion. The second domain is resistant to cellular attachment and impermeable to cells (e.g., macrophages). The biointerface membrane is made of biostable materials and may be constructed in layers, uniform or non-uniform gradients (i.e. anisotropic), or in a uniform or non-uniform cavity size configuration.

The term "domain" refers to regions of the biointerface membrane that may be layers, uniform or non-uniform gradients (e.g. anisotropic) or provided as portions of the membrane.

The term "barrier cell layer" refers to a cohesive monolayer of closely opposed cells (e.g. macrophages and foreign body giant cells) that may adhere to implanted membranes and interfere with the transport of molecules across the membrane.

The phrase "distal to" refers to the spatial relationship between various elements in comparison to a particular point of reference. For example, some embodiments of a device include a biointerface membrane having an cell disruptive domain and a cell impermeable domain. If the sensor is deemed to be the point of reference and the cell disruptive domain is positioned farther from the sensor, then that domain is distal to the sensor.

The term "proximal to" refers to the spatial relationship between various elements in comparison to a particular point of reference. For example, some embodiments of a device include a biointerface membrane having a cell disruptive domain and a cell impermeable domain. If the sensor is deemed to be the point of reference and the cell impermeable domain is positioned nearer to the sensor, then that domain is proximal to the sensor.

The term "cell processes" and the like refers to pseudopodia of a cell.

The term "solid portions" and the like refer to a material having a structure that may or may not have an open-cell configuration, but in either case prohibits whole cells from traveling through or residing within the material.

The term "substantial number" refers to the number of linear dimensions within a domain (e.g. pores or solid portions) in which greater than 50 percent of all dimensions are of the specified size, preferably greater than 75 percent and, most preferably, greater than 90 percent of the dimensions have the specified size.

The term "co-continuous" and the like refers to a solid portion wherein an unbroken curved line in three dimensions exists between any two points of the solid portion.

The term "biostable" and the like refers to materials that are relatively resistant to degradation by processes that are encountered in vivo.

The term "sensor" refers to the component or region of a device by which an analyte can be quantitated.

The term "analyte" refers to a substance or chemical constituent in a biological fluid (e.g., blood or urine) that is intended to be analyzed. A preferred analyte for measurement by analyte detection devices including the biointerface membranes of the present invention is glucose.

The terms "operably connected," "operably linked," and the like refer to one or more components being linked to another component(s) in a manner that allows transmission of signals between the components. For example, one or more electrodes may be used to detect the amount of analyte in a sample and convert that information into a signal; the signal may then be transmitted to an electronic circuit means. In this case, the electrode is "operably linked" to the electronic circuitry.

The term "electronic circuitry" refers to the components of a device required to process biological information obtained from a host. In the case of an analyte measuring device, the biological information is obtained by a sensor regarding a particular analyte in a biological fluid, thereby providing data regarding the amount of that analyte in the fluid. U.S. Pat. Nos. 4,757,022, 5,497,772 and 4,787,398 describe suitable electronic circuit means that may be utilized with devices including the biointerface membrane of the present invention.

The phrase "member for determining the amount of glucose in a biological sample" refers broadly to any mechanism (e.g., enzymatic or non-enzymatic) by which glucose can be quantitated. For example, some embodiments of the present invention utilize a membrane that contains glucose oxidase that catalyzes the conversion of oxygen and glucose to hydrogen peroxide and gluconate: Glucose+O.sub.2=Gluconate+H.sub.2O.sub.2-. Because for each glucose molecule metabolized, there is a proportional change in the co-reactant O.sub.2 and the product H.sub.2O.sub.2, one can monitor the current change in either the co-reactant or the product to determine glucose concentration.

The term "host" refers generally to mammals, particularly humans.

The term "accurately" means, for example, 90% of measured glucose values are within the "A" and "B" region of a standard Clarke error grid when the sensor measurements are compared to a standard reference measurement. It is understood that like any analytical device, calibration, calibration validation and recalibration are required for the most accurate operation of the device.

The phrase "continuous glucose sensing" refers to the period in which monitoring of plasma glucose concentration is continuously performed, for example, about every 10 minutes.

DETAILED DESCRIPTION OF THE PREFERRED EMBODIMENT

Figure 1:
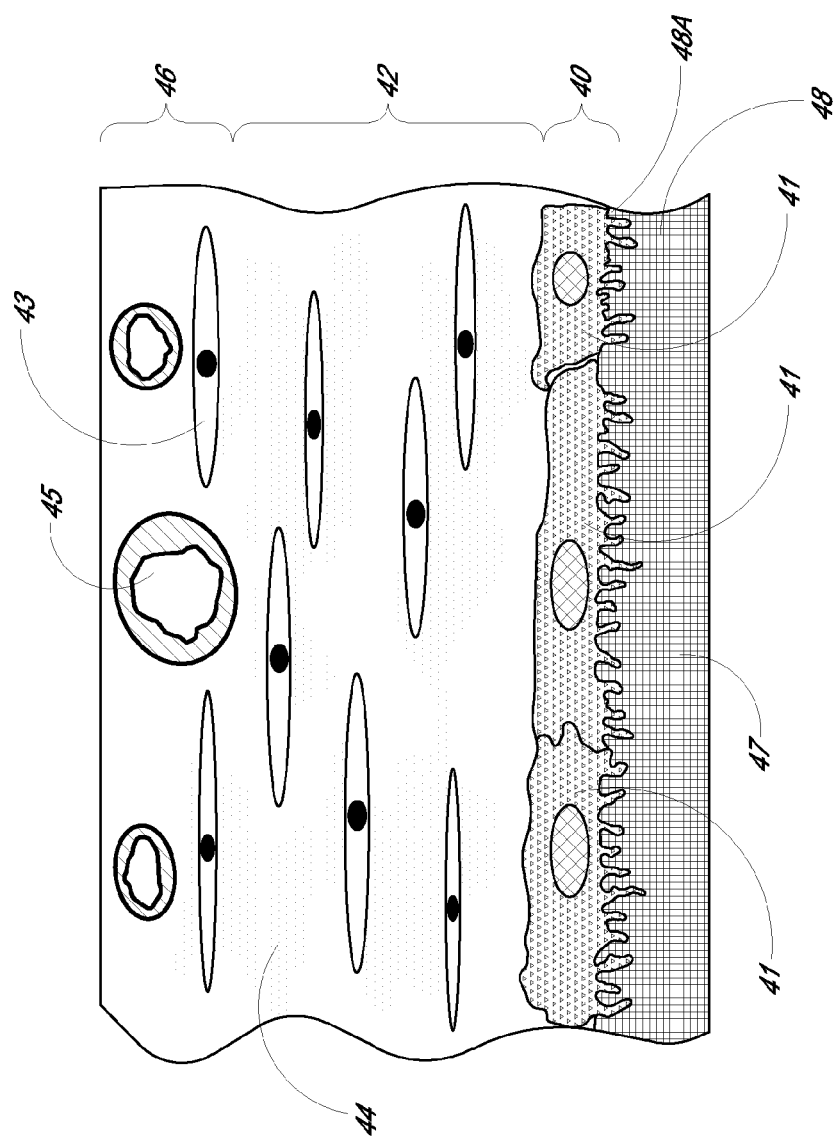
FIG. 1 is an illustration of classical three-layered foreign body response to a synthetic membrane implanted under the skin.
Figure 2:
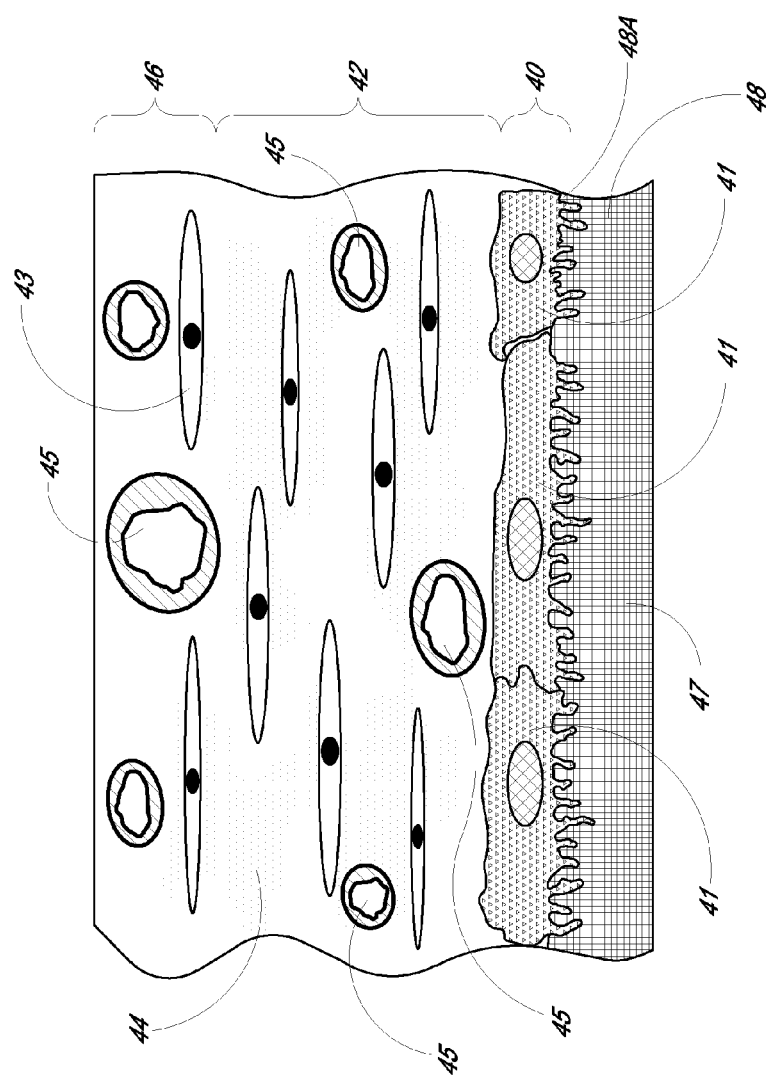
FIG. 2 is an illustration of a device having increased neovascularization within the intermediary layer of the foreign body response.

The present invention relates generally to novel biointerface membranes, their uses with implantable devices and methods for determining analyte levels in a biological fluid. More particularly, the invention provides biointerface membranes that may be utilized with implantable devices and methods for monitoring and determining glucose levels in a biological fluid, a particularly important measurement for individuals having diabetes.

Although the description that follows is primarily directed at glucose monitoring devices including the biointerface membranes of the present invention and methods for their use, these biointerface membranes are not limited to use in devices that measure or monitor glucose. Rather, these biointerface membranes may be applied to a variety of devices, including for example, those that detect and quantify other analytes present in biological fluids (including, but not limited to, cholesterol, amino acids and lactate), especially those analytes that are substrates for oxidase enzymes [see, e.g., U.S. Pat. No. 4,703,756 to Gough et al., hereby incorporated by reference] cell transplantation devices (U.S. Pat. Nos. 6,015,572, 5,964,745 and 6,083,523), drug delivery devices (U.S. Pat. Nos. 5,458,631, 5,820,589 and 5,972,369) and electrical delivery and/or measuring devices such as implantable pulse generation cardiac pacing devices (U.S. Pat. Nos. 6,157,860, 5,782,880 and 5,207,218), electrocardiogram device (U.S. Pat. Nos. 4,625,730 and 5,987,352) and electrical nerve stimulating devices (U.S. Pat. Nos. 6,175,767, 6,055,456 and 4,940,065).

Implantable devices for detecting analyte concentrations in a biological system may utilize the biointerface membranes of the present invention to interfere with the formation of a barrier cell layer, thereby assuring that the sensor receives analyte concentrations representative of that in the vasculature. Drug delivery devices may utilize the biointerface membranes of the present invention to protect the drug housed within the device from host inflammatory or immune cells that might potentially damage or destroy the drug. In addition, the biointerface membrane prevents the formation of a barrier cell layer that might interfere with proper dispensing of drug from the device for treatment of the host. Correspondingly, cell transplantation devices may utilize the biointerface membranes of the present invention to protect the transplanted cells from attack by the host inflammatory or immune response cells while simultaneously allowing nutrients as well as other biologically active molecules needed by the cells for survival to diffuse through the membrane.

The materials contemplated for use in preparing the biointerface membrane also eliminate or significantly delay biodegradation. This is particularly important for devices that continuously measure analyte concentrations. For example, in a glucose-measuring device, the electrode surfaces of the glucose sensor are in contact with (or operably connected with) a thin electrolyte phase, which in turn is covered by a membrane that contains an enzyme, e.g., glucose oxidase, and a polymer system. The biointerface membrane covers this enzyme membrane and serves, in part, to protect the sensor from external forces and factors that may result in biodegradation. By significantly delaying biodegradation at the sensor, accurate data may be collected over long periods of time (e.g. months to years). Correspondingly, biodegradation of the biointerface membrane of implantable cell transplantation devices and drug delivery devices could allow host inflammatory and immune cells to enter these devices, thereby compromising long-term function.

Devices and probes that are implanted into subcutaneous tissue will almost always elicit a foreign body capsule (FBC) as part of the body's response to the introduction of a foreign material. Therefore, implantation of a glucose sensor results in an acute inflammatory reaction followed by building of fibrotic tissue. Ultimately, a mature FBC including primarily a vascular fibrous tissue forms around the device (Shanker and Greisler, Inflammation and Biomaterials in Greco RS, ed. Implantation Biology: The Host Response and Biomedical Devices, pp 68-80, CRC Press (1994)).

In general, the formation of a FBC has precluded the collection of reliable, continuous information because it was previously believed to isolate the sensor of the implanted device in a capsule containing fluid that did not mimic the levels of analytes (e.g. glucose and oxygen) in the body's vasculature. Similarly, the composition of a FBC has prevented stabilization of the implanted device, contributing to motion artifact that also renders unreliable results. Thus, conventionally, it has been the practice of those skilled in the art to attempt to minimize FBC formation by, for example, using a short-lived needle geometry or sensor coatings to minimize the foreign body reaction.

In contrast to conventionally known practice, the teachings of the present invention recognize that FBC formation is the dominant event surrounding long-term implantation of any sensor and must be managed to support rather than hinder or block sensor performance. It has been observed that during the early periods following implantation of an analyte-sensing device, particularly a glucose sensing device, glucose sensors function well. However, after a few days to two or more weeks of implantation, these device lose their function. For example, U.S. Pat. No. 5,791,344 and Gross et al. Performance Evaluation of the Minimed Continuous Monitoring System During Patient home Use", Diabetes Technology and Therapeutics, Vol 2 Number 1, pp 49-56, 2000 have reported a glucose oxidase sensor (that has been approved for use in humans by the Food and Drug Administration) that functioned well for several days following implantation but loses function quickly after 3 days. We have observed similar device behavior with our implantable sensor. These results suggest that there is sufficient vascularization and, therefore, perfusion of oxygen and glucose to support the function of an implanted glucose sensor for the first few days following implantation. New blood vessel formation is clearly not needed for the function of a glucose oxidase mediated electrochemical sensor implanted in the subcutaneous tissue for at least several days after implantation.

We have observed that this lack of sensor function after several days is most likely due to cells, such as polymorphonuclear cells and monocytes that migrate to the wound site during the first few days after implantation. These cells consume glucose and oxygen. If there is an overabundance of such cells, they may deplete the glucose and/or oxygen before it is able to reach the sensor enzyme layer, therefore reducing the sensitivity of the device or rendering it non-functional. After the first few days, further inhibition of device function may be due to cells that associate with the membrane of the device and physically block the transport of glucose into the device (i.e. barrier cells). Increased vascularization would not be expected to overcome barrier cell blockage. The present invention contemplates the use of particular biointerface membrane architectures that interfere with barrier cell layer formation on the membrane's surface. The present invention also contemplates the use of these membranes with a variety of implantable devices (e.g. analyte measuring devices, particularly glucose measuring devices, cell transplantation devices, drug delivery devices and electrical signal delivery and measuring devices).

The sensor interface region refers to the region of a monitoring device responsible for the detection of a particular analyte. For example, in some embodiments of a glucose-monitoring device, the sensor interface refers to that region where a biological sample contacts (directly or after passage through one or more membranes or layers) an enzyme (e.g., glucose oxidase). The sensor interface region may include a biointerface membrane according to the present invention having different domains and/or layers that can cover and protect an underlying enzyme membrane and the electrodes of an implantable analyte-measuring device. In general, the biointerface membranes of the present invention prevent direct contact of the biological fluid sample with the sensor. The membranes only permit selected substances (e.g., analytes) of the fluid to pass therethrough for reaction in the immobilized enzyme domain. The biointerface membranes of the present invention are biostable and prevent barrier cell formation. The characteristics of this biointerface membrane are now discussed in more detail.

I. BIOINTERFACE MEMBRANE

Figure 3:
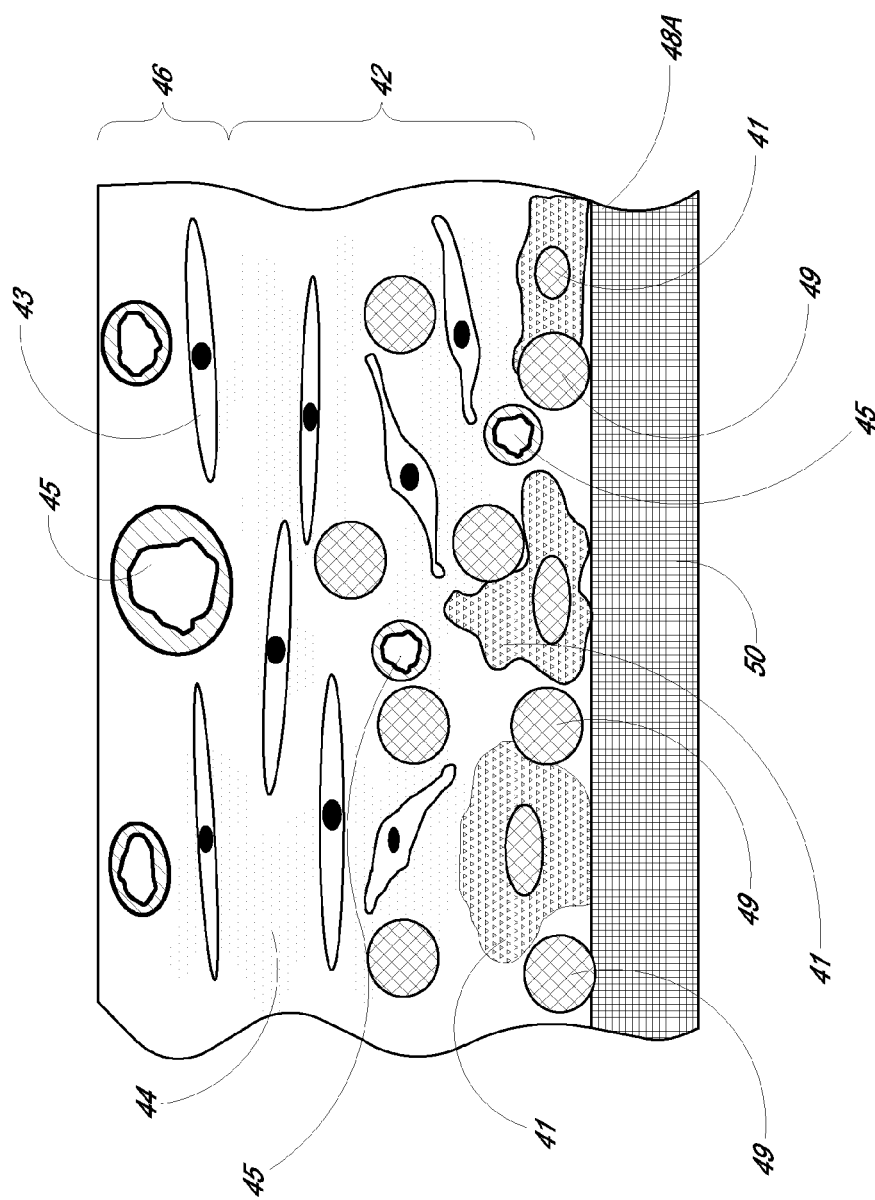
FIG. 3 is an illustration of a membrane of the present invention including a barrier-cell disruptive domain composed of fibers and a cell impermeable domain.

The biointerface membrane is constructed of two or more domains. Referring now to FIG. 3, preferably, the membrane includes a cell impermeable domain 50 proximal to an implantable device, also referred to as the second domain; and a cell disruptive domain, which in the embodiment illustrated includes non-woven fibers 49 distal to an implantable device, also referred to as the first domain.

A. Barrier-Cell Disruptive (First) Domain

Figure 4:
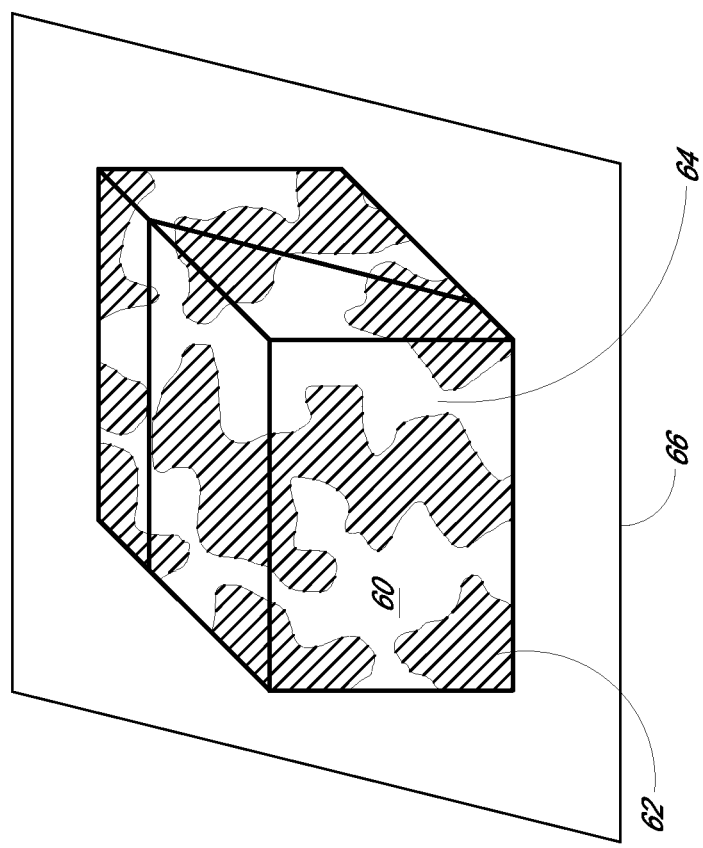
FIG. 4 is an illustration of a three dimensional section of the first domain showing the solid portions and cavities.

As described above, the outermost domain of the inventive membrane includes a material that supports tissue ingrowth. The barrier-cell disruptive domain may be composed of an open-cell configuration having cavities and solid portions. For example, FIG. 4 is an illustration of a three dimensional section 60 of a barrier-cell disruptive domain having solid portions 62 and cavities 64. Cells may enter into the cavities, however, they can not travel through or wholly exist within the solid portions. The cavities allow most substances to pass through, including, e.g., macrophages.

The open-cell configuration yields a co-continuous solid domain that contains greater than one cavity in three dimensions substantially throughout the entirety of the membrane. In addition, the cavities and cavity interconnections may be formed in layers having different cavity dimensions.

Figure 5:
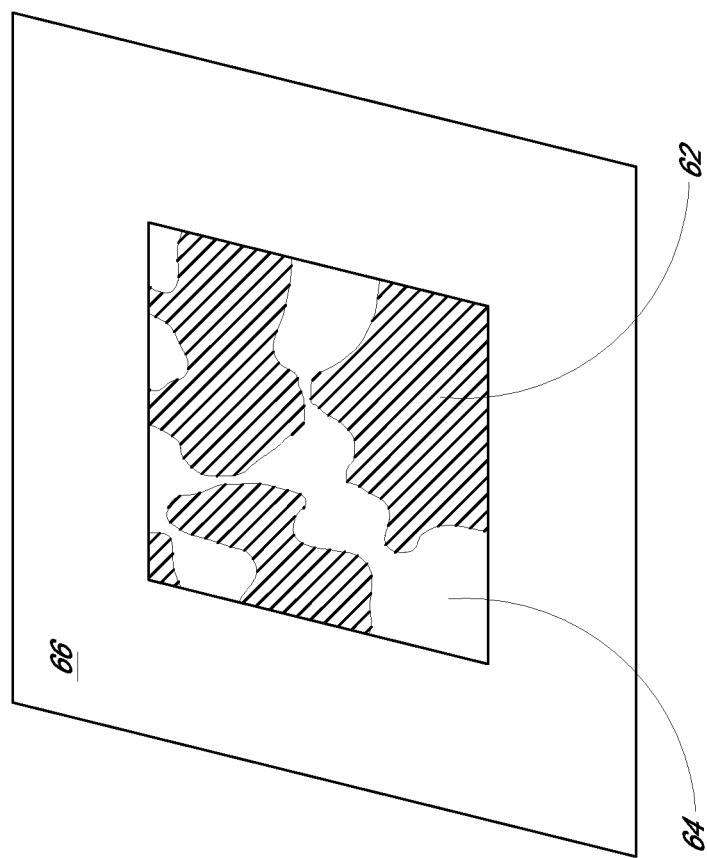
FIG. 5 is an illustration of a cross-section of the first domain in FIG. 4 showing solid portions and cavities.

In order to better describe the dimensions of cavities and solid portions, a two dimensional plane 66 cut through the barrier-cell disruptive domain can be utilized (FIG. 5). A dimension across a cavity 64 or solid portion 62 can be described as a linear line. The length of the linear line is the distance between two points lying at the interface of the cavity and solid portion. In this way, a substantial number of the cavities are not less than 20 microns in the shortest dimension and not more than 1000 microns in the longest dimension. Preferably, a substantial number of the cavities are not less than 25 microns in the shortest dimension and not more than 500 microns in the longest dimension.

Furthermore, the solid portion has not less than 5 microns in a substantial number of the shortest dimensions and not more than 2000 microns in a substantial number of the longest dimensions. Preferably, the solid portion is not less than 10 microns in a substantial number of the shortest dimensions and not more than 1000 microns in a substantial number of the longest dimensions and, most preferably, not less than 10 microns in a substantial number of the shortest dimensions and not more than 400 microns in a substantial number of the longest dimensions.

The solid portion may be comprised of polytetrafluoroethylene or polyethyleneco-tetrafluoroethylene. Preferably, the solid portion includes polyurethanes or block copolymers and, most preferably, is comprised of silicone.

In desired embodiments, the solid portion is composed of porous silicone or non-woven fibers. Non-woven fibers are preferably made from polyester or polypropylene. For example, FIG. 3 illustrates how the non-woven fibers 49 serve to disrupt the continuity of cells, such that they are not able to form a classical foreign body response. All the cell types that are involved in the formation of a FBR may be present. However, they are unable to form an ordered closely opposed cellular monolayer parallel to the surface of the device as in a typical foreign body response to a smooth surface. In this example, the 10-micron dimension provides a suitable surface for foreign body giant cells, but the fibers are in such proximity to allow and foster in growth of blood vessels 45 and vascularize the biointerface region (FIG. 3). Devices with smaller fibers have been used in previous inventions, but such membranes are prone to delamination due to the forces applied by cells in the interstices of the membrane. After delamination, cells are able to form barrier layers on the smooth or microporous surface of the bioprotective layer if it is adhesive to cells or has pores of sufficient size for physical penetration of cell processes, but not of whole cells.

When non-woven fibers are utilized as the solid portion of the present invention, the non-woven fibers may be greater than 5 microns in the shortest dimension. Preferably, the non-woven fibers are about 10 microns in the shortest dimension and, most preferably, the non-woven fibers are greater than or equal to 10 microns in the shortest dimension.

The non-woven fibers may be constructed of polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones, and block copolymers thereof including, for example, di-block, triblock, alternating, random and graft copolymers (block copolymers are discussed in U.S. Pat. Nos. 4,803,243 and 4,686,044, hereby incorporated by reference). Preferably, the non-woven fibers are comprised of polyolefins or polyester or polycarbonates or polytetrafluoroethylene. The thickness of the cell disruptive domain is not less than about 20 microns and not more than about 2000 microns.

B. Cell Impermeable (Second) Domain

The inflammatory response that initiates and sustains a FBC is associated with disadvantages in the practice of sensing analytes. Inflammation is associated with invasion of inflammatory response cells (e.g. macrophages) which have the ability to overgrow at the interface forming barrier cell layers which may block transport across the biointerface membrane. These inflammatory cells may also biodegrade many artificial biomaterials (some of which were, until recently, considered nonbiodegradable). When activated by a foreign body, tissue macrophages degranulate, releasing from their cytoplasmic myeloperoxidase system hypochlorite (bleach) and other oxidative species. Hypochlorite and other oxidative species are known to break down a variety of polymers. However, polycarbonate based polyurethanes are believed to be resistant to the effects of these oxidative species and have been termed biodurable. In addition, because hypochlorite and other oxidizing species are short-lived chemical species in vivo, biodegradation will not occur if macrophages are kept a sufficient distance from the enzyme active membrane.

The present invention contemplates the use of cell impermeable biomaterials of a few microns thickness or more (i.e., a cell impermeable domain) in most of its membrane architectures. Desirably, the thickness of the cell impermeable domain is not less than about 10 microns and not more than about 100 microns. This domain of the biointerface membrane is permeable to oxygen and may or may not be permeable to glucose and is constructed of biodurable materials (e.g. for period of several years in vivo) that are impermeable by host cells (e.g. macrophages) such as, for example, polymer blends of polycarbonate based polyurethane and PVP.

The innermost domain of the inventive membrane is non-adhesive for cells (i.e. the cell impermeable domain), which is in contrast to the inventions of Brauker et al. (supra), and Shults et al. (supra). In both of these previous patents, examples are provided in which the cellimpenetrable membrane (Brauker et al.) or biointerface membrane (Shults et al.) are derived from a membrane known as Biopore™ as a cell culture support sold by Millipore (Bedford, Mass.). In the presence of certain extracellular matrix molecules, and also in vivo, many cell types are able to strongly adhere to this membrane making it incapable of serving as a non-adhesive domain. Further, since they allow adherence of cells to the innermost layer of the membrane they promote barrier cell layer formation that decreases the membranes ability to transport molecules across the device-tissue interface. Moreover, when these cells multiply, they ultimately cause pressure between the membrane layers resulting in delamination of the layers and catastrophic failure of the membrane.

As described above, in one embodiment of the inventive membrane, the second domain is resistant to cellular attachment and is impermeable to cells and preferably composed of a biostable material. The second domain may be formed from materials such as those previously listed for the first domain and as copolymers or blends with hydrophilic polymers such as polyvinylpyrrolidone (PVP), polyhydroxyethyl methacrylate, polyvinylalcohol, polyacrylic acid, polyethers, such as polyethylene glycol, and block copolymers thereof including, for example, di-block, tri-block, alternating, random and graft copolymers (block copolymers are discussed in U.S. Pat. Nos. 4,803,243 and 4,686,044, hereby incorporated by reference).

Preferably, the second domain is comprised of a polyurethane and a hydrophilic polymer. Desirably, the hydrophilic polymer is polyvinylpyrrolidone. In one embodiment of this aspect of the invention, the second domain is polyurethane comprising not less than 5 weight percent polyvinylpyrrolidone and not more than 45 weight percent polyvinylpyrrolidone. Preferably, the second domain comprises not less than 20 weight percent polyvinylpyrrolidone and not more than 35 weight percent polyvinylpyrrolidone and, most preferably, polyurethane comprising about 27 weight percent polyvinylpyrrolidone.

As described above, in one desired embodiment the cell impermeable domain is comprised of a polymer blend comprised of a non-biodegradable polyurethane comprising polyvinylpyrrolidone. This prevents adhesion of cells in vitro and in vivo and allows many molecules to freely diffuse through the membrane. However, this domain prevents cell entry or contact with device elements underlying the membrane, and prevents the adherence of cells, and thereby prevents the formation of a barrier cell layer.

II. IMPLANTABLE GLUCOSE MONITORING DEVICES USING THE BIOINTERFACE MEMBRANES OF THE PRESENT INVENTION

The present invention contemplates the use of unique membrane architectures around the sensor interface of an implantable device. However, it should be pointed out that the present invention does not require a device including particular electronic components (e.g., electrodes, circuitry, etc). Indeed, the teachings of the present invention can be used with virtually any monitoring device suitable for implantation (or subject to modification allowing implantation); suitable devices include, analyte measuring devices, cell transplantation devices, drug delivery devices, electrical signal delivery and measurement devices and other devices such as those described in U.S. Pat. Nos. 4,703,756 and 4,994,167 to Shults et al.; U.S. Pat. No. 4,703,756 to Gough et al., and U.S. Pat. No. 4,431,004 to Bessman et al.; the contents of each being hereby incorporated by reference, and Bindra et al., Anal. Chem. 63:1692-96 (1991).

Figure 6A:
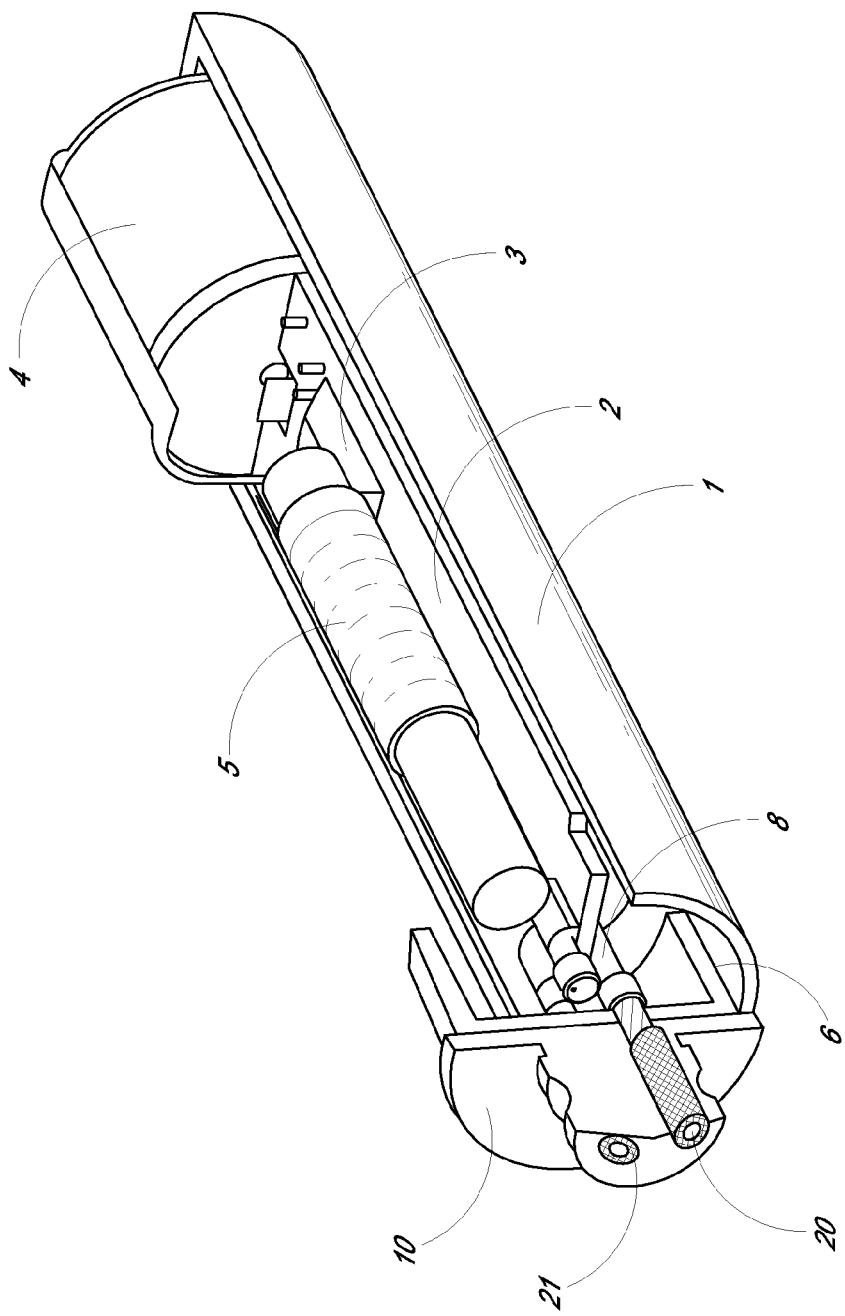
FIG. 6A depicts a cross-sectional drawing of one embodiment of an implantable analyte measuring device for use in combination with a membrane according to the present invention.

We refer now to FIG. 6A, which shows a preferred embodiment of an analyte measuring device for use in combination with a membrane according to the present invention. In this embodiment, a ceramic body 1 and ceramic head 10 houses the sensor electronics that include a circuit board 2, a microprocessor 3, a battery 4, and an antenna 5. Furthermore, the ceramic body 1 and head 10 possess a matching taper joint 6 that is sealed with epoxy. The electrodes are subsequently connected to the circuit board via a socket 8.

Figure 6B:
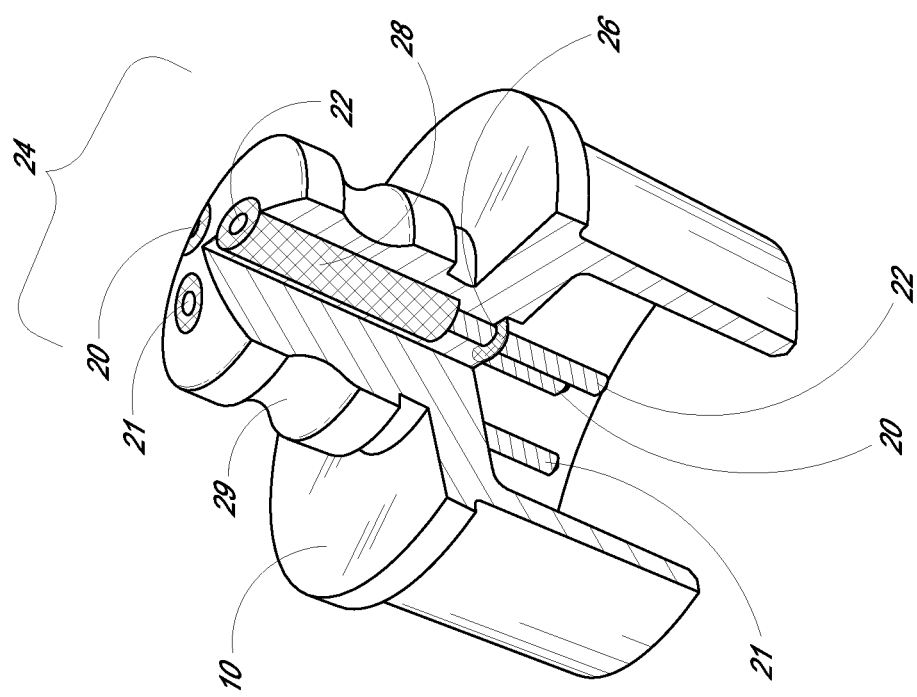
FIG. 6B depicts a cross-sectional exploded view of the sensor head shown in FIG. 6A.

As indicated in detail in FIG. 6B, three electrodes protrude through the ceramic head 10, a platinum working electrode 21, a platinum counter electrode 22 and a silver/silver chloride reference electrode 20. Each of these is hermetically brazed 26 to the ceramic head 10 and further affixed with epoxy 28. The sensing region 24 is covered with the sensing membrane described below and the ceramic head 10 contains a groove 29 so that the membrane may be affixed into place with an o-ring.

Figure 6C:
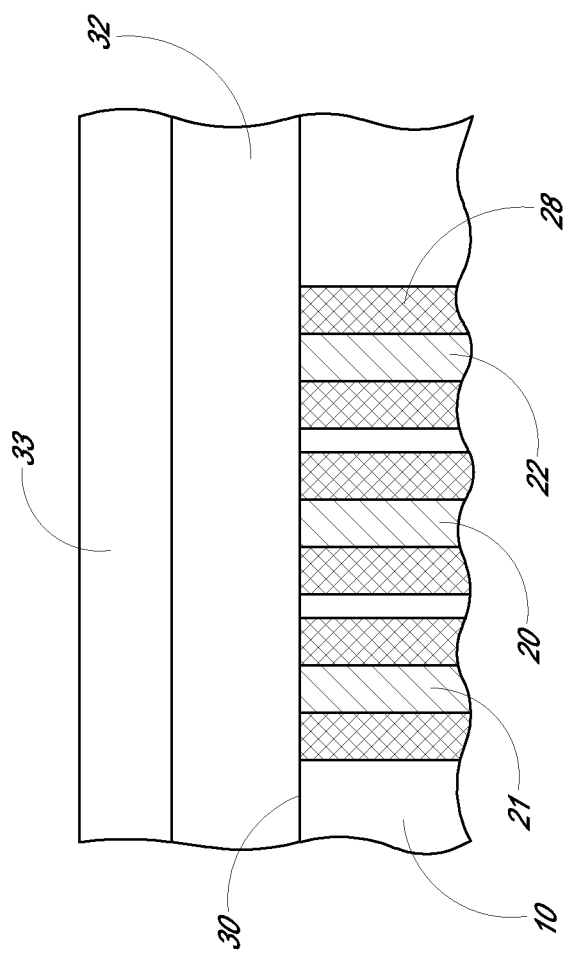
FIG. 6C depicts a cross-sectional exploded view of the electrode-membrane region set forth in FIG. 6B.

FIG. 6C depicts a cross-sectional exploded view of the electrode-membrane region 24 set forth in FIG. 6B detailing the sensor tip and the functional membrane layers. As depicted in FIG. 6C, the electrode-membrane region includes the inventive biointerface membrane 33 and a sensing membrane 32. The top ends of the electrodes are in contact with the electrolyte phase 30, a free-flowing fluid phase. The electrolyte phase is covered by the sensing membrane 32 that includes an enzyme, e.g., glucose oxidase. In turn, the inventive interface membrane 33 covers the enzyme membrane 32 and serves, in part, to protect the sensor from external forces that may result in environmental stress cracking of the sensing membrane 32.

III. EXPERIMENTAL

The following examples serve to illustrate certain preferred embodiments and aspects of the present invention and are not to be construed as limiting the scope thereof In the preceding description and the experimental disclosure which follows, the following abbreviations apply: Eq and Eqs (equivalents); mEq (milliequivalents); M (molar); mM (millimolar) .mu.M (micromolar); N (Normal); mol (moles); mmol (millimoles); .mu.mol (micromoles); nmol (nanomoles); g (grams); mg (milligrams); .mu.g (micrograms); Kg (kilograms); L (liters); mL (milliliters); dL (deciliters); .mu.L (microliters); cm (centimeters); mm (millimeters); .mu.m (micrometers); nm (nanometers); h and hr (hours); min. (minutes); s and sec. (seconds); .degree. C. (degrees Centigrade); Astor Wax (Titusville, Pa.); BASF Wyandotte Corporation (Parsippany, N.J.); Data Sciences, Inc. (St. Paul, Minn.); Douglas Hansen Co., Inc. (Minneapolis, Minn.); DuPont (DuPont Co., Wilmington, Del.); Exxon Chemical (Houston, Tex.); GAF Corporation (New York, N.Y.); Markwell Medical (Racine, Wis.); Meadox Medical, Inc. (Oakland, N.J.); Mobay (Mobay Corporation, Pittsburgh, Pa.); Sandoz (East Hanover, N.J.); and Union Carbide (Union Carbide Corporation; Chicago, Ill.).

Example 1

Preparation of Biointerface Membrane with Non-Woven Fibers

The barrier-cell disruptive domain may be prepared from a non-woven polyester fiber filtration membrane. The cell-impermeable domain may then be coated on this domain layer. The cell-impermeable domain was prepared by placing approximately 706 gm of dimethylacetamide (DMAC) into a 3L stainless steel bowl to which a polycarbonateurethane solution (1325 g, Chronoflex AR 25% solids in DMAC and a viscosity of 5100 cp) and polyvinylpyrrolidone (125 g, Plasdone K-90D) were added. The bowl was then fitted to a planetary mixer with a paddle type blade and the contents were stirred for 1 hour at room temperature. This solution was then coated on the barrier-cell disruptive domain by knife-edge drawn at a gap of 0.006" and dried at 60 .degree. C. for 24 hours. The membrane is then mechanically secured to the sensing device by an O-ring.

Example 2

Preparation of Biointerface Membrane with Porous Silicone

The barrier-cell disruptive domain can be comprised of a porous silicone sheet. The porous silicone was purchased from Seare Biomatrix Systems, Inc. The cell-impermeable domain was prepared by placing approximately 706 gm of dimethylacetamide (DMAC) into a 3L stainless steel bowl to which a polycarbonateurethane solution (1,325 gm, Chronoflex AR 25% solids in DMAC and a viscosity of 5100 cp) and polyvinylpyrrolidone (125 gm, Plasdone K-90D) were added. The bowl was then fitted to a planetary mixer with a paddle type blade and the contents were stirred for 1 hour at room temperature. The cell-impermeable domain coating solution was then coated onto a PET release liner (Douglas Hansen Co.) using a knife over roll set at a 0.012" gap. This film was then dried at 305 .degree. F. The final film was approximately 0.0015" thick. The biointerface membrane was prepared by pressing the porous silicone onto the cast cell-impermeable domain. The membrane is then mechanically secured to the sensing device by an O-ring.

Example 3

Test Method for Glucose Measuring Device Function

In vivo sensor function was determined by correlating the sensor output to blood glucose values derived from an external blood glucose meter. We have found that non-diabetic dogs do not experience rapid blood glucose changes, even after ingestion of a high sugar meal. Thus, a 10% dextrose solution was infused into the sensor-implanted dog. A second catheter is placed in the opposite leg for the purpose of blood collection. The implanted sensor was programmed to transmit at 30-second intervals using a pulsed electromagnet. A dextrose solution was infused at a rate of 9.3 ml/minute for the first 25 minutes, 3.5 ml/minute for the next 20 minutes, 1.5 ml/minute for the next 20 minutes, and then the infusion pump was powered off Blood glucose values were measured in duplicate every five minutes on a blood glucose meter (LXN Inc., San Diego, Calif.) for the duration of the study. A computer collected the sensor output. The data was then compiled and graphed in a spreadsheet, time aligned, and time shifted until an optimal R-squared value was achieved. The R-squared value reflects how well the sensor tracks with the blood glucose values.

Example 4

In Vivo Evaluation of Glucose Measuring Devices Including the Biointerface Membranes of the Present Invention To test the importance of a cell-disruptive membrane, implantable glucose sensors comprising the biointerface membranes of the present invention were implanted into dogs in the subcutaneous tissues and monitored for glucose response on a weekly basis. Control devices comprising only a cell-impermeable domain ("Control") were compared with devices comprising a cell-impermeable domain and a barrier-cell disruptive domain, in particular, wherein the barrier-cell disruptive domain was either a non-woven fiber ("Non-Woven Fibers") or porous silicone ("Porous Silicone").

Figure 7:
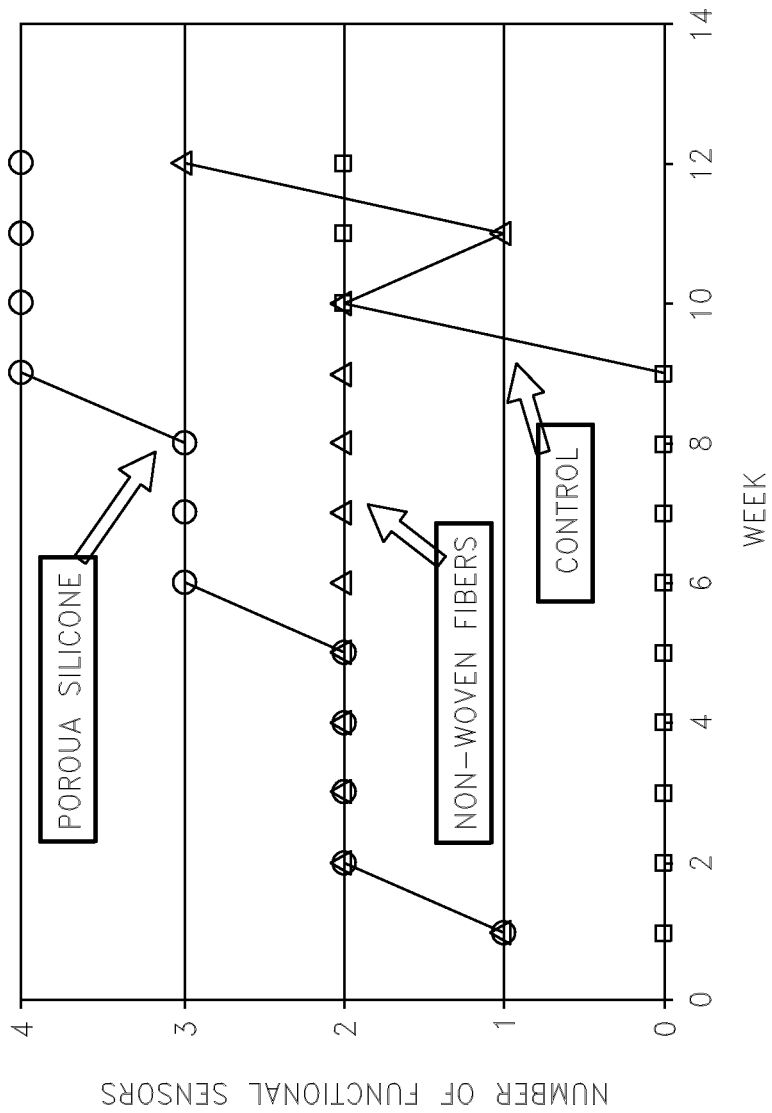
FIG. 7 is a graphical representation of the number of functional sensors versus time (i.e. weeks) comparing control devices including only a cell-impermeable domain ("Control"), with devices including a cell-impermeable domain and a barrier-cell domain, in particular, wherein the barrier-cell disruptive domain includes non-woven fiber ("Non-Woven Fibers") and wherein the barrier-cell disruptive domain includes porous silicone ("Porous Silicone").

Four devices from each condition were implanted subcutaneously in the ventral abdomen of normal dogs. On a weekly basis, the dogs were infused with glucose as described in Example 3 in order to increase their blood glucose levels from about 120 mg/dl to about 300 mg/dl. Blood glucose values were determined with a LXN blood glucose meter at 5-minute intervals. Sensor values were transmitted at 0.5-minute intervals. Regression analysis was done between blood glucose values and the nearest sensor value within one minute. Devices that yielded an R-squared value greater than 0.5 were considered functional. FIG. 7 shows, for each condition, the number of functional devices over the 12-week period of the study. Both test devices performed better than the control devices over the first 9 weeks of the study. All of the porous silicone devices were functional by week 9. Two of 4 polypropylene fiber devices were functional by week 2, and 3 of 4 were functional on week 12. In contrast, none of the control devices were functional until week 10, after which 2 were functional for the remaining 3 weeks. These data clearly show that the use of a cell-disruptive layer in combination with a cell-impermeable layer improves the function of implantable glucose sensors.

The description and experimental materials presented above are intended to be illustrative of the present invention while not limiting the scope thereof It will be apparent to those skilled in the art that variations and modifications can be made without departing from the spirit and scope of the present invention.

What is claimed is:

1. An implantable device for continuous measurement of a glucose concentration, comprising:
    a sensing region configured to continuously measure a signal indicative of a glucose concentration in a host; and
    a membrane located over the sensing region, wherein the membrane comprises a first layer and a second layer, wherein the first layer comprises an enzyme configured to catalyze a reaction with glucose as a reactant, wherein the second layer is formed of a blend comprising a polyurethane polymer and an acrylate polymer.

2. The implantable device of claim 1, wherein the polyurethane polymer is a copolymer, wherein the copolymer comprises silicone.

3. The implantable device of claim 1, wherein the acrylate polymer comprise methacrylate.

4. The implantable device of claim 1, wherein the membrane is configured to facilitate obtaining of a level of accuracy corresponding to having, over a period of time exceeding 5 days, 90% of measured analyte values within an "A" region and a "B" region of a standard Clarke error grid when sensor measurements are compared to a standard reference measurement.

5. The implantable device of claim 1, wherein the membrane has a thickness of from about 10 microns to about 100 microns.

6. The implantable device of claim 1, wherein the membrane is configured to provide an interface with an interstitial fluid.

7. The implantable device of claim 1, wherein the membrane is configured to prevent barrier cell formation.

\* \* \* \* \*

UNITED STATES PATENT AND TRADEMARK OFFICE
CERTIFICATE OF CORRECTION

PATENT NO. : 9,532,741 B2  
APPLICATION NO. : 14/341468  
DATED : January 3, 2017  
INVENTOR(S) : James H. Brauker et al.

Page 1 of 3

It is certified that error appears in the above-identified patent and that said Letters Patent is hereby corrected as shown below:

On the Title Page

In Column 1 (page 6, item (56)) at Line 4, Under Other Publications, change "elemetry" to --telemetry--.

In Column 1 (page 6, item (56)) at Line 19, Under Other Publications, change "a" to --at--.

In Column 1 (page 6, item (56)) at Line 24, Under Other Publications, change "meaurement." to --measurement.--.

In Column 1 (page 6, item (56)) at Line 31, Under Other Publications, change "glocuse" to --glucose--.

In Column 1 (page 6, item (56)) at Line 39, Under Other Publications, change "Cylic" to --Cyclic--.

In Column 1 (page 6, item (56)) at Line 40, Under Other Publications, change "Curent" to --Current--.

In Column 1 (page 6, item (56)) at Line 50, Under Other Publications, change "Braucker" to --Brauker--.

In Column 1 (page 6, item (56)) at Line 52, Under Other Publications, change "surfacts" to --Surfactants--.

In Column 1 (page 6, item (56)) at Line 59, Under Other Publications, after "from" delete "the".

In Column 1 (page 6, item (56)) at Line 65, Under Other Publications, change "measuement" to --measurement--.

Signed and Sealed this  
Fifth Day of September, 2017

Joseph Matal  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 9,532,741 B2

In Column 2 (page 6, item (56)) at Line 12, Under Other Publications, after "for" insert --the--.

In Column 2 (page 6, item (56)) at Line 15, Under Other Publications, change "childen" to --children--.

In Column 2 (page 6, item (56)) at Line 28, Under Other Publications, change "voltarmmetry:" to --voltammetry:--.

In Column 2 (page 6, item (56)) at Line 55, Under Other Publications, change "applicaions." to --applications.--.

In Column 1 (page 7, item (56)) at Line 16, Under Other Publications, change "Tensions" to --Tension--.

In Column 1 (page 7, item (56)) at Line 58, Under Other Publications, change "Technolog" to --Technology--.

In Column 2 (page 7, item (56)) at Line 9, Under Other Publications, change "-288." to -- -588.--.

In Column 1 (page 8, item (56)) at Line 9, Under Other Publications, change "an" to --and--.

In Column 1 (page 8, item (56)) at Line 9, Under Other Publications, change "biotelemeter" to --biotelemetry--.

In Column 2 (page 8, item (56)) at Line 2, Under Other Publications, change "microfabicated" to --microfabricated--.

In Column 2 (page 8, item (56)) at Line 10, Under Other Publications, change "Beioelectronics" to --Bioelectronics--.

In Column 2 (page 8, item (56)) at Line 44, Under Other Publications, change "2(3)59-65." to --2(3):59-65.--.

In Column 2 (page 8, item (56)) at Line 68, Under Other Publications, change "fabricataed" to --fabricated--.

In Column 1 (page 9, item (56)) at Line 6, Under Other Publications, change "amperometeric" to --amperometric--.

In Column 1 (page 9, item (56)) at Line 25, Under Other Publications, change "glucoseoxidse-based" to --glucoseoxidase-based--.

In Column 1 (page 9, item (56)) at Line 40, Under Other Publications, change

CERTIFICATE OF CORRECTION (continued)
U.S. Pat. No. 9,532,741 B2

"Plytetrafluoroethylene" to --Polytetrafluoroethylene--.

In Column 1 (page 9, item (56)) at Line 58, Under Other Publications, change "termistor" to --thermistor--.

In Column 2 (page 9, item (56)) at Line 40, Under Other Publications, change "Applciations" to --Applications--.

In Column 2 (page 10, item (56)) at Line 12, Under Other Publications, change "or" to --for--.

In Column 2 (page 10, item (56)) at Line 70, Under Other Publications, change "Clinial" to --Clinical--.

In Column 1 (page 11, item (56)) at Line 48, Under Other Publications, change "E nzymatic" to --Enzymatic--.

In Column 2 (page 11, item (56)) at Line 17, Under Other Publications, change "evaluaton." to --evaluation.--.

In Column 2 (page 11, item (56)) at Line 52, Under Other Publications, change "applicablilty" to --applicability--.

In Column 2 (page 12, item (56)) at Line 18, Under Other Publications, change "Butyrul" to --Butyryl--.

In Column 2 (page 12, item (56)) at Line 18, Under Other Publications, change "angioge3nesis" to --angiogenesis--.

In the Drawings

Sheet 9 of 9 (Y-axis, FIG. 7) at Line 1, Change "POROUA" to --POROUS--.

In the Specification

In Column 10 at Lines 61-62, Change "cellimpenetrable" to --cell impenetrable--.

In Column 12 at Line 14, Change "o-ring." to --O-ring.--.

In Column 12 at Line 33, After "thereof" insert --.--.

In Column 14 at Line 33, After "thereof" insert --.--.